US008685372B2

(12) United States Patent
Tsien et al.

(10) Patent No.: US 8,685,372 B2
(45) Date of Patent: Apr. 1, 2014

(54) PEPTIDES AND APTAMERS FOR TARGETING OF NEURON OR NERVES

(75) Inventors: Roger Y. Tsien, La Jolla, CA (US); Quyen T. Nguyen, Del Mar, CA (US); Michael Whitney, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/264,512

(22) PCT Filed: Apr. 15, 2010

(86) PCT No.: PCT/US2010/031231
§ 371 (c)(1),
(2), (4) Date: Feb. 29, 2012

(87) PCT Pub. No.: WO2010/121023
PCT Pub. Date: Oct. 21, 2010

(65) Prior Publication Data
US 2012/0148499 A1 Jun. 14, 2012

Related U.S. Application Data

(60) Provisional application No. 61/169,626, filed on Apr. 15, 2009.

(51) Int. Cl.
*A61K 49/00* (2006.01)
*G01N 33/53* (2006.01)
*A61P 25/00* (2006.01)
*C07K 19/00* (2006.01)
*C07K 17/02* (2006.01)
*A61K 38/18* (2006.01)
*C07K 7/08* (2006.01)
*C07K 17/10* (2006.01)

(52) U.S. Cl.
USPC ............ 424/9.6; 530/327; 530/323; 530/399; 435/7.1; 514/17.7; 514/8.4; 514/8.5

(58) Field of Classification Search
None
See application file for complete search history.

(56) References Cited

U.S. PATENT DOCUMENTS

| 2004/0253243 A1 | 12/2004 | Epstein et al. |
| 2006/0228420 A1 | 10/2006 | Martin |
| 2007/0197444 A1 | 8/2007 | Herman et al. |
| 2007/0243554 A1 | 10/2007 | Jagota et al. |

FOREIGN PATENT DOCUMENTS

WO WO 2006/105392 A2 10/2006

OTHER PUBLICATIONS

International Search Report mailed on Jan. 3, 2011, for International Patent Application No. PCT/US2010/031231 filed Apr. 15, 2010, 3 pages.
Köbbert, C. et al,, "Current concepts in neuroanatomical tracing," *Progress in Neurobiology*, 2000, vol. 62, pp. 327-351.
Marangos, N . et al. "In vivo visualization of the cochlear nerve and nuclei with fluorescent axonal tracers," *Hearing Research*, 2001, vol. 162, pp. 48-52.
O'Malley, M.R. et al., "Fluorescent Retrograde Axonal Tracing of the Facial Nerve," *The Laryngoscope*, 2006, vol. 116, pp. 1792-1797.
Richmond, F.J.R. et al., "Efficacy of seven retrograde tracers, compared in multiple-labelling studies of feline motoneurones," *Journal of Neuroscience Methods*, 1994, vol. 53, pp. 35-46.
Supplementary European Search Report for EP Application No. 10765180.4 mailed Oct. 30, 2012, 3 pages.
Whitney, M.A. et al., "Fluorescent peptides highlight peripheral nerves during surgery in mice," *Nature Biotechnology*, Apr. 2011, vol. 29, No. 4, pp. 353-356, Online Methods, 2 pages.

*Primary Examiner* — Cecilia J Tsang
*Assistant Examiner* — Tara Martinez
(74) *Attorney, Agent, or Firm* — Morgan, Lewis & Bockius LLP

(57) ABSTRACT

The present invention provides methods for guiding preservation of neurons or nerves during surgery by administering a fluorescently-labeled peptide or aptamer that specifically binds to the neurons or nerves. The invention further provides targeting molecules of fluorescently-labeled peptides or aptamers that specifically bind to neurons or nerves and for compositions thereof.

17 Claims, 9 Drawing Sheets

PEPTIDES AND APTAMERS FOR TARGETING OF NEURON OR NERVES

CROSS-REFERENCES TO RELATED APPLICATIONS

This application claims priority to U.S. Provisional Application Ser. No. 61/169,626, filed Apr. 15, 2009, the disclosure of which is incorporated herein by reference in its entirety for all purposes.

STATEMENT AS TO RIGHTS TO INVENTIONS MADE UNDER FEDERALLY SPONSORED RESEARCH OR DEVELOPMENT

This invention was made with Government Support under NIH Grant Nos. NS27177 and K08 EB008122-01. The Government has certain rights in the invention.

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The central nervous system (CNS) consists of the brain and the spinal cord, as well as the retina.

The peripheral nervous system (PNS) extends outside the CNS. The PNS is divided into the somatic nervous system and the autonomic nervous system.

A neuron is an electrically excitable cell that processes and transmits information by electrical and chemical signaling. A typical neuron possesses a cell body (often called the soma), dendrites, and an axon.

A nerve is an enclosed, cable-like bundle of neural axons. Each nerve is a cordlike structure that contains many axons.

Each axon is surrounded by a layer of tissue called the endoneurium. The axons are bundled together into groups called fascicles, and each fascicle is wrapped in a layer of tissue called the perineurium. The neuron or nerve is wrapped in a layer of tissue called the epineurium.

BRIEF SUMMARY OF THE INVENTION

Disclosed herein, in certain embodiments, are targeting molecules comprising a peptide or aptamer that specifically binds to a neuron, nerve, or component of either. In some embodiments, the peptide is selected from: AHHNSWKAKHHS (SEQ ID NO:1), TYTDWLNFWAWP (SEQ ID NO:2), KSLSRHDHIHHH (SEQ ID NO:3), NTQTLAKAPEHT (SEQ ID NO:4), DFTKTSPLGIH (SEQ ID NO:5), LTPIPLPTPKPP (SEQ ID NO:6), VSTMPMSNMNGP (SEQ ID NO:7), GIFERNFGAMLH(SEQ ID NO:8), ACLREYHNWC (SEQ ID NO:9), MHRQPIAPVSSL (SEQ ID NO:10), SFADPLLFLAPP (SEQ ID NO:11), ASAHHMFTPGFD (SEQ ID NO:12), VAPTKAPLHSPS (SEQ ID NO:13), NNLKTGTSAPTG (SEQ ID NO:14), HKTAQWPFIAFR (SEQ ID NO:15), RLTNAPAYQAPA (SEQ ID NO:16), MQNPLNGKPGR (SEQ ID NO:17), THYSRSLTDGTR(SEQ ID NO:18), FSTSNNQSSPAI (SEQ ID NO:19), YPSPNRPPNLTN(SEQ ID NO:20), DIANPPPPPLYV (SEQ ID NO:21), ALQTDGPFAESA (SEQ ID NO:22), DNAQHSERFPVP (SEQ ID NO:23), and IPPTFPDRIRAPG (SEQ ID NO:24). In some embodiments, the targeting molecule further comprises a drug. In some embodiments, the targeting molecule further comprises a drug selected from: an antihistamine, a GABA receptor modulator, a neurotransmitter reuptake inhibitor, a local anesthetic, an anticholinergic, a sodium channel blocker, a calcium channel blocker, a thyrotropin-releasing hormone, a γ-secretase inhibitor, an AMPA receptor agonist or antagonist, an NMDA receptor agonist or antagonist, an mGlu receptor agonist or antagonist, a growth factor, an antiemetic agent, a corticosteroid; a cytotoxic agent; an antioxidant, an iron chelator, a mitochondrial modulator, a sirtuin modulator, a nitric oxide (NO) and/or nitric oxide synthase (NOS) modulator, a potassium channel agonist or antagonist, a purigenic receptor agonist or antagonist, or a combination thereof. In some embodiments, the targeting molecule further comprises a drug selected from: benzocaine; carticaine; cinchocaine; cyclomethycaine; lidocaine; prilocaine; propxycaine; proparacaine; tetracaine; tocainide; and trimecaine; methotrexate; cyclophosphamide; thalidomide; paclitaxel; pemetrexed; pentostatin; pipobroman; pixantrone; plicamycin; procarbazine; raltitrexed; rebeccamycin; rubitecan; SN-38; salinosporamide A; satraplatin; streptozotocin; swainsonine; tariquidar; taxane; tegafur-uracil; temozolomide; testolactone; thioTEPA; tioguanine; topotecan; trabectedin; tretinoin; triplatin tetranitrate; tris(2-chloroethyl)amine; troxacitabine; uracil mustard; valrubicin; vinblastine; vincristine; vinorelbine; vorinostat; zosuquidar; carbamazepine; oxcarbazepine; phenytein; valproic acid; sodium valproate; cinnarizine; flunarizine; nimodipine; brain-derived neurotrophic factor (BDNF); ciliary neurotrophic factor (CNTF); glial cell-line derived neurotrophic factor (GDNF); neurotrophin-3; neurotrophin-4; fibroblast growth factor (FGF) receptor; insulin-like growth factor (IGF); or a combination thereof In some embodiments, the targeting molecule further comprises a fluorescent moiety. In some embodiments, the targeting molecule further comprises a fluorescent moiety selected from: a fluorescent protein, a fluorescent peptide, a fluorescent dye, or a combination thereof. In some embodiments, the targeting molecule further comprises a fluorescent moiety selected from: a xanthene; a bimane; a coumarin; an aromatic amines; a benzofuran; a fluorescent cyanine; a carbazole; a dicyanomethylene pyrane; polymethine; oxabenzanthrane; pyrylium; carbostyl; perylene; acridone; quinacridone; rubrene; anthracene; coronene; phenanthrecene; pyrene; butadiene; stilbene; porphyrin; pthalocyanine; lanthanide metal chelate complexes; rare-earth metal chelate complexes; and derivatives thereof. In some embodiments, the targeting molecule further comprises a fluorescent moiety selected from: 5-carboxyfluorescein; fluorescein-5-isothiocyanate; 6-carboxyfluorescein; tetramethylrhodamine-6-isothiocyanate; 5-carboxytetramethylrhodamine; 5-carboxy rhodol derivatives; tetramethyl and tetraethyl rhodamine; diphenyldimethyl and diphenyldiethyl rhodamine; dinaphthyl rhodamine; rhodamine 101 sulfonyl chloride; Cy3, Cy3B, Cy3.5, Cy5, Cy5.5, Cy 7, indocyanine green, IR800CW or combinations thereof.

Disclosed herein, in certain embodiments, are methods of identifying a neuron or nerve, comprising contacting a neuron or nerve with a targeting molecule comprising (a) a peptide or an aptamer that specifically binds to a neuron, nerve, or component of either, and (b) a fluorescent moiety. In some embodiments, the peptide is selected from: AHHNSWKAKHHS (SEQ ID NO:1), TYTDWLNFWAWP (SEQ ID NO:2), KSLSRHDHIHHH (SEQ ID NO:3), NTQTLAKAPEHT (SEQ ID NO:4), DFTKTSPLGIH (SEQ ID NO:5), LTPIPLPTPKPP (SEQ ID NO:6), VSTMPMSNMNGP (SEQ ID NO:7), GIFERNFGAMLH (SEQ LD NO:8), ACLREYHNWC (SEQ ID NO:9), MHRQPIAPVSSL (SEQ ID NO:10), SFADPLLFLAPP (SEQ ID NO:11), ASAHHM-FTPGFD (SEQ ID NO:12), VAPTKAPLHSPS (SEQ ID NO:13), NNLKTGTSAPTG (SEQ ID NO:14), HKTAQWP-FIAFR (SEQ ID NO:15), RLTNAPAYQAPA (SEQ ID NO:16), MQNPLNGKPGR (SEQ ID NO:17), THYSRSLTDGTR (SEQ ID NO:18), FSTSNNQSSPAI (SEQ ID NO:19), YPSPNRPPNLTN (SEQ ID NO:20), DIANPPPPPLYV (SEQ ID NO:21), ALQTDGPFAESA (SEQ ID NO:22), DNAQHSERFPVP (SEQ ID NO:23), and IPPTFPDRIRAPG (SEQ ID NO:24). In some embodiments, the fluorescent moiety is selected from: a fluorescent protein, a fluorescent peptide, a fluorescent dye, or a combination thereof. In some embodiments, the fluorescent moiety is selected from: a xanthene; a bimane; a coumarin; an aromatic amines; a benzofuran; a fluorescent cyanine; a carbazole; a dicyanomethylene pyrane; polymethine; oxabenzanthrane; pyrylium; carbostyl; perylene; acridone; quinacridone; rubrene; anthracene; coronene; phenanthrecene; pyrene; butadiene; stilbene; porphyrin; pthalocyanine; lanthanide metal chelate complexes; rare-earth metal chelate complexes; and derivatives thereof. In some embodiments, the fluorescent moiety is selected from: 5-carboxyfluorescein; fluorescein-5-isothiocyanate; 6-carboxyfluorescein; tetramethylrhodamine-6-isothiocyanate; 5-carboxytetramethylrhodamine; 5-carboxy rhodol derivatives; tetramethyl and tetraethyl rhodamine; diphenyldimethyl and diphenyldiethyl rhodamine; dinaphthyl rhodamine; rhodamine 101 sulfonyl chloride; Cy3, Cy3B, Cy3.5, Cy5, Cy5.5, Cy 7, indocyanine green, IR800CW or combinations thereof.

Disclosed herein, in certain embodiments, are methods of delivering a drug to a neuron or nerve, comprising contacting a neuron or nerve with a targeting molecule comprising (a) a peptide or an aptamer that specifically binds to a neuron, nerve, or component of either, and (b) a drug. In some embodiments, the peptide is selected from: AHHNSWKA-KHHS (SEQ ID NO:1), TYTDWLNFWAWP (SEQ ID NO:2), KSLSRHDHIHHH (SEQ ID NO:3), NTQT-LAKAPEHT (SEQ ID NO:4), DFTKTSPLGIH (SEQ ID NO:5), LTPIPLPTPKPP (SEQ ID NO:6), VSTMPMSNM-NGP (SEQ ID NO:7), GIFERNFGAMLH (SEQ ID NO:8), ACLREYHNWC (SEQ ID NO:9), MHRQPIAPVSSL (SEQ ID NO:10), SFADPLLFLAPP (SEQ ID NO:11), ASAHHM-FTPGFD (SEQ ID NO:12), VAPTKAPLHSPS (SEQ ID NO:13), NNLKTGTSAPTG (SEQ ID NO:14), HKTAQWP-FIAFR (SEQ ID NO:15), RLTNAPAYQAPA (SEQ ID NO:16), MQNPLNGKPGR (SEQ ID NO:17), THYSRSLTDGTR (SEQ ID NO:18), FSTSNNQSSPAI (SEQ ID NO:19), YPSPNRPPNLTN (SEQ ID NO:20), DIANPPPPPLYV (SEQ ID NO:21), ALQTDGPFAESA (SEQ ID NO:22), DNAQHSERFPVP (SEQ ID NO:23), and IPPTFPDRIRAPG (SEQ ID NO:24). In some embodiments, the drug is selected from: an antihistamine, a GABA receptor modulator, a neurotransmitter reuptake inhibitor, a local anesthetic, an anticholinergic, a sodium channel blocker, a calcium channel blacker, a thyrotropin-releasing hormone, a γ-secretase inhibitor, an AMPA receptor agonist or antagonist, an NMDA receptor agonist or antagonist, an mGlu receptor agonist or antagonist, a growth factor, an antiemetic agent, a corticosteroid; a cytotoxic agent; an antioxidant, an iron chelator, a mitochondrial modulator, a sirtuin modulator, a nitric oxide (NO) and/or nitric oxide synthase (NOS) modulator, a potassium channel agonist or antagonist, a purigenic receptor agonist or antagonist, or a combination thereof. In some embodiments, the drug is selected from: benzocaine; carticaine; cinchocaine; cyclomethycaine; lidocaine; prilocaine; propxycaine; proparacaine; tetracaine; tocainide; and trimecaine; methotrexate; cyclophosphamide; thalidomide; paclitaxel; pemetrexed; pentostatin; pipobroman; pixantrone; plicamycin; procarbazine; raltitrexed; rebeccamycin; rubitecan; SN-38; salinosporamide A; satraplatin; streptozotocin; swainsonine; tariquidar; taxane; tegafururacil; temozolomide; testolactone; thioTEPA; tioguanine; topotecan; trabectedin; tretinoin; triplatin tetranitrate; tris(2-chloroethyl)amine; troxacitabine; uracil mustard; valrubicin; vinblastine; vincristine; vinorelbine; vorinostat; zosuquidar; carbamazepine; oxcarbazepine; phenytein; valproic acid; sodium valproate; cinnarizine; flunarizine; nimodipine; brain-derived neurotrophic factor (BDNF); ciliary neurotrophic factor (CNTF); glial cell-line derived neurotrophic factor (GDNF); neurotrophin-3; neurotrophin-4; fibroblast growth factor (FGF) receptor; insulin-like growth factor (IGF); or a combination thereof.

Disclosed herein, in certain embodiments, are pharmaceutical compositions comprising: (a) a peptide or aptamer that specifically binds to a neuron, nerve, or component of either, and (b) a pharmaceutically acceptable excipient. In some embodiments, the peptide is selected from: AHHNSWKA-KHHS (SEQ ID NO:1), TYTDWLNFWAWP (SEQ ID NO:2), KSLSRHDHIHHH (SEQ ID NO:3), NTQT-LAKAPEHT (SEQ ID NO:4), DFTKTSPLGIH (SEQ ID NO:5), LTPTLPTPKPP (SEQ ID NO:6), VSTMPMSNM-NGP (SEQ ID NO:7), GIFERNFGAMLH (SEQ ID NO:8), ACLREYHNWC (SEQ ID NO:9), MHRQPIAPVSSL (SEQ ID NO:10), SFADPLLFLAPP (SEQ ID NO: 11), ASAHH-MFTPGFD (SEQ ID NO:12), VAPTKAPLHSPS (SEQ ID NO:13), NNLKTGTSAPTG (SEQ ID NO:14), HKTAQWP-FIAFR (SEQ ID NO:15), RLTNAPAYQAPA (SEQ ID NO:16), MQNPLNGKPGR (SEQ ID NO:17), THYSRSLTDGTR (SEQ ID NO:18), FSTSNNQSSPAI (SEQ ID NO:19), YPSPNRPPNLTN (SEQ ID NO:20), DIANPPPPPLYV (SEQ ID NO:21), ALQTDGPFAESA (SEQ ID NO:22), DNAQHSERFPVP (SEQ ID NO:23), and IPPTFPDRIRAPG (SEQ ID NO:24). In some embodiments, the peptide or aptamer is bound to a drug. In some embodiments, the peptide or aptamer is bound to a fluorescent moiety.

DETAILED DESCRIPTION OF THE INVENTION

Introduction

Figure 1:
FIG. 1. Peptide labeling of nerves. Fluorescence images of exposed sciatic nerves in living wild-type mice following administration of (A-B) acetyl-SHSNTQTLAKAPEHTGK (5,6FAM)-amide (SEQ ID NO:25) derived from the ex vivo screen or (C) a control peptide acetyl-SHSSTARDLWPH-GKEGK(5,6FAM)-amide (SEQ ID NO:26). K(5,6FAM)-amide is the $N^\epsilon$-[fluorescein-5(6)-carbonyl]-lysinamide at the C-terminus.

Preservation of neurons and nerves is one of the most important goals of any surgical procedure, because accidental transection of neuron or nerves leads to significant morbidity. Nerves are typically identified by their elongated whitish appearance and relationship to nearby structures or by electrophysiological studies. However, in instances such as trauma, tumor involvement, inflammation, or infection, nerve identification using these criteria can be difficult. Therefore, there is a need for methods of reliably and conclusively identifying neuron or nerves which overcome the deficiencies in the art.

Neuron or nerve identification prior to direct exposure during surgery or confirmation of neuron or nerve identity in instances of uncertainty following direct exposure is accomplished by electromyographic (EMG) monitoring. This technique, however, has the disadvantage of not providing visual feedback to the operating surgeon. Thus, even if a nerve has been identified in one location, either through accidental or purposeful stimulation, there is no visual guidance to the operating surgeon as to how far away from the stimulation site the nerve lies or the direction of travel the nerve takes away from the stimulation site. Furthermore, EMG only traces motor pathways, not sensory fibers. EMG fails if neuron or nerve conduction or neuromuscular transmission is temporarily blocked anywhere distal to the recording site. Such blockade easily occurs due to neuron or nerve compression, trauma, local anesthetics, or neuromuscular blockers.

Neuron or nerve labeling primarily depend on retrograde or anterograde tracing of individually identified axonal tracts via the use of fluorescent dyes. However, methods of labeling neuron or nerves by locally applied fluorescent tracers have several disadvantages. First, this technique can label only one neuron or nerve fiber tract at a time, depending on where the dye has been injected. Second, this technique results in only limited labeling of fluorescent dyes along the axonal tracts, because retrograde axonal tracers typically accumulate in the neural cell body. Third, retrograde transport is relatively slow (on the order of millimeters per day) and therefore takes a long time to label human neuron or nerves, which are often longer than a meter, such as in the case of the sciatic neuron or nerve and its arborizations. Fourth, the application of fluorescent dyes to innervation targets such as direct intramuscular injections to label motor neuron or nerves is typically messy with a variable amount of the tracer dye remaining at the injection site. As dissection of neuron or nerves depends on accurate visualization of adjacent structures prior to encountering them, a surgical site that is contaminated with fluorescent dyes would not be desirable. Finally, the direct injection of the fluorescent dye itself may be damaging to the target organs or neuron or nerve of interest, either by mechanical damage or by the very high local concentration of dye and vehicle at the injection site.

DEFINITIONS

As used herein, the following terms have the meanings ascribed to them unless specified otherwise.

As used herein, the term "targeting molecule" refers to any agent (e.g., peptide, protein, nucleic acid polymer, aptamer, or small molecule) that specifically binds to a target of interest. The target of interest may be a tissue, a cell type, a cellular structure (e.g., an organelle), a protein, a peptide, a polysaccharide, or a nucleic acid polymer. In some embodiments, the targeting molecule is any agent that specifically binds to one or more neurons or nerves of a subject.

As used herein, the term "aptamer" refers to a DNA or RNA molecule that has been selected from random pools based on their ability to bind other molecules with high affinity specificity based on non-Watson and Crick interactions with the target molecule (see, e.g., Cox and Ellington, *Bioorg. Med. Chem.* 9:2525-2531 (2001); Lee et al., *Nuc. Acids Res.* 32:D95-D100 (2004)). Aptamers can be selected which bind nucleic acid, proteins, small organic compounds, vitamins, inorganic compounds, cells, and even entire organisms.

The terms "polypeptide," "peptide," and "protein" are used interchangeably herein to refer to a polymer of amino acid residues. The terms apply to naturally occurring occurring amino acid polymers as well as amino acid polymers in which one or more amino acid residues is a non-naturally occurring amino acid (e.g., an amino acid analog). The terms encompass amino acid chains of any length, including full length proteins (i.e., antigens), wherein the amino acid residues are linked by covalent peptide bonds. As used herein, the term "peptide" refers to a polymer of amino acid residues typically ranging in length from 2 to about 50 residues. In certain embodiments the peptide ranges in length from about 2, 3, 4, 5, 7, 9, 10, or 11 residues to about 50, 45, 40, 45, 30, 25, 20, or 15 residues. In certain embodiments the peptide ranges in length from about 8, 9, 10, 11, or 12 residues to about 15, 20 or 25 residues. Where an amino acid sequence is provided herein, L-, D-, or beta amino acid versions of the sequence are also contemplated as well as retro, inversion, and retro-inversion isoforms. Peptides also include amino acid polymers in which one or more amino acid residues is an artificial chemical analogue of a corresponding naturally occurring amino acid, as well as to naturally occurring amino acid polymers. In addition, the term applies to amino acids joined by a peptide linkage or by other modified linkages (e.g., where the peptide bond is replaced by an α-ester, a β-ester, a thioamide, phosphonamide, carbamate, hydroxylate, and the like (see, e.g., Spatola, (1983) *Chem. Biochem. Amino Acids and Proteins* 7: 267-357), where the amide is replaced with a saturated amine (see, e.g., Skiles et al., U.S. Pat. No. 4,496,542, which is incorporated herein by reference, and Kaltenbronn et al., (1990) Pp. 969-970 in Proc. 11th American Peptide Symposium, ESCOM Science Publishers, The Netherlands, and the like)).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

One of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

As used herein, the terms "label" refers to a molecule that facilitates the visualization and/or detection of a targeting molecule disclosed herein. In some embodiments, the label is a fluorescent moiety.

The phrase "specifically binds" when referring to the interaction between a targeting molecule disclosed herein and a target (e.g., purified protein, neuron or nerve tissue, neuron or nerves, cranial neuron or nerves, central neuron or nerves, myelinated or unmyelinated neuron or nerves, or connective tissue surrounding neuron or nerves), refers to the formation of a high affinity bond between the targeting molecule and the target. Further, the term means that the targeting molecule has low affinity for non-targets.

"Selective binding," "selectivity," and the like refer to the preference of agent to interact with one molecule as compared to another. Preferably, interactions between a targeting molecule disclosed herein and a target are both specific and selective. Note that in some embodiments an agent is designed to "specifically bind" and "selectively bind" two distinct, yet similar targets without binding to other undesirable targets.

The terms "individual," "patient," or "subject" are used interchangeably. As used herein, they mean any mammal (i.e. species of any orders, families, and genus within the taxonomic classification animalia: chordata: vertebrata: mammalia). In some embodiments, the mammal is a human. None of the terms require or are limited to situation characterized by the supervision (e.g. constant or intermittent) of a health care worker (e.g. a doctor, a registered nurse, a nurse practitioner, a physician's assistant, an orderly, or a hospice worker).

The terms "administer," "administering", "administration," and the like, as used herein, refer to the methods that may be used to enable delivery of agents or compositions to the desired site of biological action. These methods include, but are not limited to parenteral injection (e.g., intravenous, subcutaneous, intraperitoneal, intramuscular, intravascular, intrathecal, intravitreal, infusion, or local). Administration techniques that are optionally employed with the agents and methods described herein, include e.g., as discussed in Goodman and Gilman, The Pharmacological Basis of Therapeutics, current ed.; Pergamon; and Remington's, Pharmaceutical Sciences (current edition), Mack Publishing Co., Easton, Pa.

The team "pharmaceutically acceptable" as used herein, refers to a material that does not abrogate the biological activity or properties of the agents described herein, and is relatively nontoxic (i.e., the toxicity of the material significantly outweighs the benefit of the material). In some instances, a pharmaceutically acceptable material may be administered to an individual without causing significant undesirable biological effects or significantly interacting in a deleterious manner with any of the components of the composition in which it is contained.

The term "surgery" as used herein, refers to any methods for that may be used to manipulate, change, or cause an effect by a physical intervention. These methods include, but are not limited to open surgery, endoscopic surgery, laparoscopic surgery, minimally invasive surgery, robotic surgery, any procedures that may affect any neuron or nerves such as placement of retractors during spinal surgery, cardiac neuron or nerve ablation, epidural injection, intrathecal injections, neuron or nerve blocks, implantation of devices such as neuron or nerve stimulators and implantation of pumps.

Targets

Disclosed herein, in certain embodiments, are targeting molecules that specifically bind to a target.

In some embodiments, the target is a neuron or nerve. The nerve is any nerve (e.g., motor nerves, sensory nerves, sympathetic and parasympathetic nerves, periprostatic neurovascular bundle, sciatic nerves, cranial nerves including olfactory nerve, optic nerve, oculomotor nerve, trochlear nerve, trigeminal nerve, abducens nerve, facial nerve, vestibulocochlear nerve, glossopharyngeal nerve, vagus nerve, accessory nerve, hypoglossal nerve, spinal nerves, brachial plexus, or lumbrosacral plexus). The neuron is any neuron (e.g., sensory neurons (afferent neurons), motor neurons (efferent neurons), interneurons, unipolar neurons, bipolar neurons, multipolar neurons, basket cells, Betz cells, medium spiny neurons, Purkinje cells, pyramidal cells, Renshaw cells, Granule cells, anterior horn cells). In some embodiments, the neuron or nerve is myelinated. In some embodiments, the neuron or nerve is unmyelinated. In some embodiments, the neuron or nerve is demyelinated. In some embodiments, the neuron or nerve is undergoing demyelination.

In some embodiments, the target is a component of a neuron or nerve. The component of a neuron or nerve is any component of a neuron or nerve. In some embodiments, the target is tissue within or surrounding a neuron or nerve (e.g., epineurium, perineurium, or endoneurium). In some embodiments, the target is a component of myelin, (e.g., myelin basic protein (MBP), myelin oligodendrocyte glycoprotein, or proteolipid protein). In some embodiments, the target is expressed by Schwann cells, (e.g., MBP, glial fibrillary acidic protein, S-100, or myelin protein zero). In some embodiments, the target is a component of neuron or nerve tissue, (e.g., elastin, fibrillin, e-cadherin, cytokeratin, vimentin, collagen I, collagen, III, collagen IV, or collagen V). In some embodiments, the target is a neurotrophic factor receptor expressed in neuron or nerves, (e.g., tyrosine kinase receptors TrkA, TrkB, and TrkC, low affinity neuron or nerve growth receptor or p75 neurotrophin receptor, or GDNF family receptor alpha-1 or -2). In some embodiments, the target is a non-neurotrophic factor receptor expressed in a neuron or nerve tissue, (e.g., epithelial growth factor receptors, transforming growth factor beta receptors, vascular endothelial growth factor receptors, endothelin A receptors, endothelin B receptors, and integrin receptors).

Determining whether a targeting molecule is capable of binding a neuron or nerve or component thereof is accomplished by any suitable method. In some embodiments, the method of determining whether a targeting molecule is capable of binding a neuron or nerve or component thereof involves contacting a targeting molecule (e.g., peptide or aptamer) disclosed herein with a test agent for a period of time sufficient to allow the targeting molecule and test agent to form a binding complex. The binding complex is detected using any suitable method. Suitable binding assays can be performed in vitro or in vivo and include, but are not limited to, phage display, two-hybrid screens, co-precipitation, cross-linking, and expression cloning (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61-89. Other binding assays involve the use of mass spectrometry or NMR techniques to identify molecules bound to the target of interest. The targeting molecule utilized in such assays can be naturally expressed, cloned or synthesized.

In some embodiments, the targeting molecule is capable of crossing the blood-brain barrier in order to reach reach and bind the neuron or nerve of interest.

Targeting Molecules

Peptides and Aptamers

In some embodiments, the targeting molecule comprises a peptide sequence selected from: AHHNSWKAKHHS (SEQ ID NO:1), TYTDWLNFWAWP (SEQ ID NO:2), KSLSRHDHIHHH (SEQ ID NO:3), NTQTLAKAPEHT (SEQ ID NO:4), DFTKTSPLGIH (SEQ ID NO:5), LTPIPLPTPKPP (SEQ ID NO:6), VSTMPMSNMNGP (SEQ ID NO:7), GIFERNFGAMLH(SEQ ID NO:8), ACLREYHNWC(SEQ ID NO:9), MHRQPIAPVSSL (SEQ ID NO:10), SFADPLLFLAPP (SEQ ID NO:11), ASAHHMFTPGFD (SEQ ID NO:12), VAPTKAPLHSPS (SEQ ID NO:13), NNLKTGTSAPTG (SEQ ID NO:14), HKTAQWPFIAFR (SEQ ID NO:15), RLTNAPAYQAPA (SEQ ID NO:16), MQNPLNGKPGR (SEQ ID NO:17), THYSRSLTDGTR, (SEQ ID NO:18), FSTSNNQSSPAI (SEQ ID NO:19), YPSPNRPPNLTN (SEQ ID NO:20), DIANPPPPPLYV (SEQ ID NO:21), ALQTDGPFAESA (SEQ ID NO:22), DNAQHSERFPVP (SEQ ID NO:23), and IPPTFPDRIRAPG (SEQ ID NO:24).

In some embodiments, the targeting molecule comprises a peptide sequence sharing 80% homology with a peptide sequence disclosed herein. In some embodiments, the targeting molecule comprises a peptide sequence sharing 85% homology with a peptide sequence disclosed herein. In some embodiments, the targeting molecule comprises a peptide sequence sharing 90% homology with a peptide sequence disclosed herein. In some embodiments, the targeting molecule comprises a peptide sequence sharing 95% homology with a peptide sequence disclosed herein. In some embodiments, the targeting molecule comprises a peptide sequence sharing 99% homology with a peptide sequence disclosed herein.

In some embodiments, the targeting molecule comprises an aptamer.

The peptides and aptamers of the present invention are synthesized by any suitable method. For example, targeting peptides and aptamers of the present invention can be chemically synthesized by solid phase peptide synthesis. Techniques for solid phase synthesis are described, for example, by Barany and Merrifield (1963) *Solid-Phase Peptide Synthesis;* pp. 3-284 *in The Peptides: Analysis, Synthesis, Biology. Vol. 2: Special Methods in Peptide Synthesis, Part A.*; Merrifield et al. (1963) *J. Am. Chem. Soc.,* 85: 2149-2156, and Stewart et al. (1984) *Solid Phase Peptide Synthesis,* 2nd ed. Pierce Chem. Co., Rockford, Ill.

Cargo

In some embodiments, the targeting molecule further comprises a cargo. In some embodiments, the peptide or aptamer is directly bound to a cargo. In some embodiments, the peptide or aptamer is indirectly (e.g., via a linker) bound to a cargo. In some embodiments, two or more peptides or aptamers are directly or indirectly bound to a cargo. In some embodiments, the cargo is a drug. In some embodiments, the cargo is a fluorescent moiety.

Drugs

In some embodiments, the targeting molecule further comprises a drug. All drugs that act on a neuron or nerve (or a component thereof) are encompassed within the term "drug." Specific examples of drug given herein, are illustrative and are not meant to limit the drugs for use with the targeting molecules disclosed herein.

In some embodiments, the peptide or aptamer is directly bound to a drug. In some embodiments, the peptide or aptamer is indirectly (e.g., via a linker) bound to a drug. In some embodiments, two or more peptides or aptamers are directly or indirectly bound to a drug.

In some embodiments, the drug is selected from a drug that: induces cell death (apoptotic or necrotic), inhibits cell death (apoptotic or necrotic), inhibits the transmission of a neuron or nerve signal (i.e., an electrochemical impulse), inhibits the release of a neurotransmitter, agonizes the activity of a GABA receptor, partially or fully inhibits the repolarization of a neuron, disrupts the conduction of an ion channel, or a combination thereof.

In some embodiments, the drug is an antihistamine, a GABA receptor modulator, a neurotransmitter reuptake inhibitor, a local anesthetic, an anticholinergic, a sodium channel blocker, a calcium channel blocker, a thyrotropin-releasing hoinione, a γ-secretase inhibitor, an AMPA receptor agonist or antagonist, an NMDA receptor agonist or antagonist, an mGlu receptor agonist or antagonist, a growth factor, an antiemetic agent, a corticosteroid; a cytotoxic agent; an antioxidant, an iron chelator, a mitochondrial modulator, a sirtuin modulator, a nitric oxide (NO) and/or nitric oxide synthase (NOS) modulator, a potassium channel agonist or antagonist, a purigenic receptor agonist or antagonist, or a combination thereof.

In some embodiments, the drug is meclizine, diphenhydramine, dimenhydrinate, loratadine, quetiapine, mepyramine, piperoxan, antazoline, carbinoxamine, doxylamine, clemastine, pheniramine, chlorphenamine, chlorpheniramine, dexchlorpheniramine, brompheniramine, triprolidine, cyclizine, chlorcyclizine, hydroxyzine, promethazine, alimemazine, trimeprazine, cyproheptadine, azatadine, ketotifen, oxatomide, meclizine hydrochloride, promethazine hydrochloride, cinnarizine, hydroxyzine pamoate, betahistine dihydrochloride, alprazolam, bromazepam, brotizolam, chlordiazepoxide, clonazepam, clorazepate, diazepam, estazolam, flunitrazepam, flurazepam, loprazolam, lorazepam, lormetazepam, idazolam, nimetazepam, nitrazepam, oxazepam, prazepam, temazepam, triazolam, clonazepam, diazepam, lorazepam, furosemide, bumetanide, ethacrynic acid, gabapentin, pregabalin, muscimol, baclofen, amitriptyline, nortriptyline, trimipramine, fluoxetine, paroxetine, sertraline, glycopyrrolate, homatropine, scopolamine, atropine, benzocaine, carticaine, cinchocaine, cyclomethycaine, lidocaine, prilocaine, propxycaine, proparacaine, tetracaine, tocainide, trimecaine, carbamazepine, oxcarbazepine, phenytein, valproic acid, sodium valproate, cinnarizine, flunarizine, nimodipine, thyrotropin-releasing hormone, amifostine (also known as WR-2721, or ETHYOL®); a carbamate compound (e.g., 2-phenyl-1,2-ethanediol monocarbomates and dicarbamates); LY450139 (hydroxylvaleryl monobenzocaprolactam); L685458 (1S-benzyl-4R [1-[1-S-carbamoyl-2-phenethylcarbamoyl)-1S-3-methylbutylcarbamoyl]-2R-hydroxy-5-phenylpentyl}carbamic acid tert-butyl ester); LY411575 ($N^2$-[(2S)-2-[(3,5-difluorophenyl)-2-hydroxyethanoyl]-N [(7S)-5-methyl-6-oxo-6,7-dihydro-5H-dibenzo[bid]azepin-7yl]-L-alaninamide);
MK-0752; tarenflurbil; BMS-299897 (2-[(1R)-1-[[(4-chlorophenyl)sulfony](2,5-difluorophenyl)amino]ethyl]-5-fluorobenzenepropanoic acid; CNQX (6-cyano-7-nitroquinoxaline-2,3-dione); NBQX (2,3-dihydroxy-6-nitro-7-sulfamoylbenzo[f]quinoxaline-2,3-dione); DNQX (6,7-dinitroquinoxaline-2,3-dione); kynurenic acid; 2,3-dihydroxy-6-nitro-7-sulfamoylbenzo-[f]quinoxaline;
1-aminoadamantane; dextromethorphan; dextrorphan; ibogaine; ketamine; nitrous oxide; phencyclidine; riluzole; tiletamine; memantine; dizocilpine; aptiganel; remacimide; 7-chlorokynurenate; DCKA (5,7-dichlorokynurenic acid); kynurenic acid; 1-aminocyclopropanecarboxylic acid (ACPC); AP7 (2-amino-7-phosphonoheptanoic acid); APV (R-2-amino-5-phosphonopentanoate); CPPene (3-[(R)-2-carboxypiperazin-4-yl]-prop-2-enyl-1-phosphonic acid); (+)-(1S,2S)-1-(4-hydroxy-phenyl)-2-(4-hydroxy-4-phenylpiperidino)-1-pro-panol; (1S,2S)-1-(4-hydroxy-3-methoxyphenyl)-2-(4-hydroxy-4-phenylpiperi-dino)-1-propanol; (3R,4S)-3-(4-(4-fluorophenyl)-4-hydroxypiperidin-1-yl-)-chroman-4;7-diol; (1R*,2R*)-1-(4-hydroxy-3-methylphenyl)-2-(4-(4-fluoro-phenyl)-4-hydroxypiperidin-1-yl)-propan-1-ol-mesylate); LY389795 ((−)-2-thia-4-aminobicyclo-hexane-4,6-dicarboxylate); LY379268 ((−)-2-oxa-4-aminobicyclo-hexane-4,6-dicarboxylate); LY354740 ((+)-2-aminobicyclo-hexane-2,6dicarboxylate); DCG-IV ((2S,2'R,3'R)-2-(2',3'-dicarboxycyclopropyl)glycine); 2R,4R-APDC (2R,4R-4-aminopyrrolidine-2,4-dicarboxylate); (S)-3C4HPG ((S)-3-carboxy-4-hydroxyphenylglycine); (S)-4C3HPG ((S)-4-carboxy-3-hydroxyphenylglycine); L-CCG-I ((2S,1'S,2S)-2-(carboxycyclopropyl)glycine); ACPT-I ((1S,3R,4S)-1-aminocyclopentane-1,3,4-tricarboxylic acid); L-AP4 (L-(+)-2-Amino-4-phosphonobutyric acid); (S)-3,4-DCPG ((S)-3,4-dicarboxyphenylglycine); (RS)-3,4-DCPG ((RS)-3,4-dicarboxyphenylglycine); (RS)-4-phosphonophenylglycine ((RS)PPG); AMN082 (,N'-bis(diphenylmethyl)-1,2-ethanediamine dihydrochloride); DCG-IV ((2S,2'R,3'R)-2-(2',3"-dicarboxycyclopropyl)glycine); AMN082; brain-derived neurotrophic factor (BDNF); ciliary neurotrophic factor (CNTF); glial cell-line derived neurotrophic factor (GDNF); neurotrophin-3; neurotrophin-4; fibroblast growth factor (FGF) receptor; insulin-like growth factor (IGF); an aminoglycoside antibiotic (e.g., gentamicin and amikacin); a macrolide antibiotic (e.g, erythromycin); a glycopeptide antibiotic (e.g. vancomycin); salicylic acid; nicotine; Eburnamenine-14-carboxylic acid ethyl ester; sipatrigine (2-(4-Methylpiperazin-1-yl)-5-(2,3,5-trichlorophenyl)-pyrimidin-4-amine); amiloride (3,5-diamino-N-(aminoiminomethyl)-6-chloropyrazinecarboxamide hydrochloride); carbamazepine (5H-dibenzo[b,f]azepine-5-carboxamide); TTX (octahydro-12-(hydroxymethyl)-2-imino-5,9;7,10a-dimethano-10aH-[1,3]dioxocino[6,5-d] pyrimidine-4,7,10,11,12-pen tot); RS100642 (1-(2,6-dimethyl-phenoxy)-2-ethylaminopropane hydrochloride); mexiletine ((1-(2,6-dimethylphenoxy)-2-aminopropane hydrochloride)); QX-314 (N-(2,6-Dimethylphenylcarbamoylmethyl)triethylammonium bromide); phenyloin (5,5-diphenylimidazolidine-2,4-dione); lamotrigine (6-(2,3-dichlorophenyl)-1,2,4-triazine-3,5-diamine); 4030W92 (2,4-diamino-5-(2,3-dichlorophenyl)-6-fluoromethylpyrimidine); BW1003C87 (5-(2,3,5-trichlorophenyl)pyrimidine-2,4-1.1 ethanesulphonate); QX-222 (2-[(2,6-dimethylphenyl)amino]-N,N,N-trimethyl-2-oxoethanaminium chloride); ambroxol (trans-4-[[(2-Amino-3,5-dibromophenyl)methyl]amino]cyclo hexanol hydrochloride); R56865 (N-[1-(4-(4-fluorophenoxy)butyl]-

4-piperidinyl-N-methyl-2-benzo-thiazolamine); lubeluzole; ajmaline ((17R,21alpha)-ajmalan-17,21-diol); procainamide (4-amino-N-(2-diethylaminoethyl)benzamide hydrochloride); flecainide; riluzoleor; triamicinolone actenoide; Dexamethasone; promethazine; prochlorperazine; trimethobenzamide; triethylperazine; dolasetron; granisetron; ondansetron; tropisetron; and palonosetron; droperidol; meclizine; perphenazine; thiethyl perazine; domperidone; properidol; haloperidol; chlorpromazine; promethazine; prochlorperazine; metoclopramide; dronabinol; nabilone; sativex; scopolamine; dexamethasone; trimethobenzamine; emetrol; propofol; muscimol; acridine carboxamide; actinomycin; 17-N-allylamino-17-demethoxygeldanamycin; amsacrine; aminopterin; anthracycline; antineoplastic; antineoplaston; 5-azacytidine; azathioprine; BL22; bendamustine; biricodar; bleomycin; bortezomib; bryostatin; busulfan; calyculin; camptothecin; capecitabine; carboplatin; chlorambucil; cisplatin; cladribine; clofarabine; cytarabine; dacarbazine; dasatinib; daunorubicin; decitabine; dichloroacetic acid; discodermolide; docetaxel; doxorubicin; epirubicin; epothilone; eribulin; estramustine; etoposide; exatecan; exisulind; ferruginol; floxuridine; fludarabine; fluorouracil; fosfestrol; fotemustine; gemcitabine; hydroxyurea; IT-101; idarubicin; ifosfamide; imiquimod; irinotecan; irofulven; ixabepilone; laniquidar; lapatinib; lenalidomide; lomustine; lurtotecan; mafosfamide; masoprocol; mechlorethamine; melphalan; mercaptopurine; mitomycin; mitotane; mitoxantrone; nelarabine; nilotinib; oblimersen; oxaliplatin; PAC-1; methotrexate (RHEUMATREX®, Amethopterin); cyclophosphamide (CYTOXAN™); thalidomide (THALIDOMID®); paclitaxel; pemetrexed; pentostatin; pipobroman; pixantrone; plicamycin; procarbazine; proteasome inhibitors (e.g.; bortezomib); raltitrexed; rebeccamycin; rubitecan; SN-38; salinosporamide A; satraplatin; streptozotocin; swainsonine; tariquidar; taxane; tegafur-uracil; temozolomide; testolactone; thioTEPA; tioguanine; topotecan; trabectedin; tretinoin; triplatin tetranitrate; tris(2-chloroethyl)amine; troxacitabine; uracil mustard; valrubicin; vinblastine; vincristine; vinorelbine; vorinostat; zosuquidar; N-acetylcysteine; vitamin E; vitamin C; vitamin A; lutein; selenium glutathione; melatonin; a polyphenol; a carotenoid; coenzyme Q-10; Ebselen (2-phenyl-1,2-benzisoselenazol-3 (2H)-one (also called PZ 51 or DR3305); L-methionine; azulenyl nitrones; L-(+)-Ergothioneine; CAPE (caffeic acid phenethyl ester); dimethylthiourea; dimethylsulfoxide; disufenton sodium; pentoxifylline; MCI-186; Ambroxol; U-83836E; MitoQ (mitoquinone mesylate); Idebenone (2-(10-hydroxydecyl)-5,6-dimethoxy-3-methyl-cyclohexa-2,5-diene-1,4-drone); desferrioxamine; hydroxybenzyl ethylene diamine; fullerenol-1, pyrrolidine dithiocarbamate; acetylcarnitine; lipoic acid; a stilbene; a chalcone; a flavone; an isoflavone; a flavanones; an anthocyanidin; a catechin; isonicotinamide; dipyridamole; ZM 336372; camptothecin; coumestrol; nordihydroguaiaretic acid; esculetin; SRT-1720; SRT-1460; SRT-2183; aminoguanidine; 1-Amino-2-hydroxyguanidine p-toluensulfate; GED; bromocriptine mesylate; dexamethasone; SDMA; ADMA; L-NMMA; L-NMEA; D-MMA; L-NIL; L-NNA; L-NPA; L-NAME; L-VNIO; diphenyleneiodonium chloride; 2-ethyl-2-thiopseudourea; haloperidol; L-NIO; MEG; SMT; SMTC; 7-Ni; nNOS inhibitor; 1,3-PBITU; L-thiocitrulline; TRIM; MTR-105; BBS-1; BBS-2; ONO-1714; GW273629; GW 274150; PPA250; AR-R17477; AR-R18512; spiroquinazolone; 1400W; S-NC; NTG; SNP; thapsigargin; VEGF; bradykinin; ATP; sphingosine-1-phosphate; estrogen; angiopoietin; acetylcholine; SIN-1; GEA 3162; GEA; GEA 5024; GEA 5538; SNAP; molsidomine; CNO-4; CNO-5; DEA/NO; IPA/NO; SPER/ NO; SULFI/NO; OXI/NO; DETA/NO; nicorandil; minoxidil, leveromakalim; lemakalim; cromakalim; L-735,334; retigabine; flupirtine; BMS-204352; DMP-543; linopirdine; XE991; 4-AP; 3,4-DAP; E-4031; DIDS; Way 123,398; CGS-12066A; dofetilide; sotalol; apamin; amiodarone; azimilide; bretylium; tedisamil; ibutilide; sematilide; nifekalant; tamulustoxin; ATP; ADP; UTP; UDP; UDP-glucose; adenosine; 2-MESATP; 2-MESADP; ABMEATP; DATPAS; ATPFS; BZ-ATP; MRS2703; DENUFOSOL TETRASODIUM; MRS2365; MRS 2690; PSB 0474; A-317491; RO-3 (Roche); SURAMIN; PPADS; PPNDS; DIDS; pyridoxal-5-phosphate; 5-(3-bromophenyl)-1,3-dihydro-2H-benzofuro-[3,2-e]-1,4-diazepin-2-one; cibacron. blue; basilen blue; ivermectin; A-438079; A-740003; NF023; NF449; NF110; NF157; MRS 2179; NF279; MRS 2211; MRS 2279; MRS 2500 tetrasodium salt; TNP-ATP; tetramethylpyrazine; $Ip_5I$; βγ-carboxymethylene ATP; βγ-chlorophosphomethylene ATP; KN-62; spinorphin; minocycline; SB-203580 (4-(4-Fluorophenyl)-2(4-methylsulfinyl phenyl)-5-(4-pyridyl)1H-imidazole); PD 169316 (4-(4-Fluorophenyl)-2-(4-nitrophenyl)-5-(4-pyridyl)-1H-imidazole); SB 202190 (4-(4-Fluorophenyl)-2-(4-hydroxyphenyl)-5-(4-pyridyl)1H-imidazole); RWJ 67657 (4-[4-(4-fluorophenyl)-1-(3-phenylpropyl)-5-(4-pyridinyl)-1H-imidazol-2-yl]-3-butyn-1-ol); SB 220025 (5-(2-Amino-4-pyrimidinyl)-4-(4-fluorophenyl)-1-(4-piperidinlyl)imidazole); D-JNKI-1 ((D)-$hJIP_{175-157}$-DPro-DPro-(D)-HIV-$TAT_{57-48}$); AM-111 (Auris); SP600125 (anthra[1,9-cd]pyrazol-6(2H)-one); JNK Inhibitor I ((L)-HIV-$TAT_{48-57}$-PP-$JBD_{20}$); JNK Inhibitor III ((L)-HIV-$TAT_{47-57}$-gaba-c-$Junδ_{33-57}$); AS601245 (1,3-benzothiazol-2-yl (2-[[2-(3-pyridinyl)ethyl]amino]-4 pyrimidinyl)acetonitrile); JNK Inhibitor VI ($H_2N$-RPKRPTTLNLF-$NH_2$) (SEQ ID NO:32); JNK Inhibitor VIII (N-(4-Amino-5-cyano-6-ethoxypyridin-2-yl)-2-(2,5-dimethoxyphenyl) acetamide); JNK Inhibitor IX (N-(3-Cyano-4,5,6,7-tetrahydro-1-benzothien-2-yl)-1-naphthamide); dicumarol (3,3'-Methylenebis(4-hydroxycoumarin)); SC-2:36 (4-[5-(4-chlorophenyl)-3-(trifluoromethyl)-1H-pyrazol-1-yl] benzene-sulfonamide); CEP-1347 (Cephalon); CEP-11004 (Cephalon); an artificial protein comprising at least a portion of a Bcl-2 polypeptide; a recombinant FNK; V5 (also known as Bax inhibitor peptide V5); Bax channel blocker ((±)-1-(3, 6-Dibromocarbazol-9-yl)-3-piperazin-1-yl-propan-2-ol); Bax inhibiting peptide P5 (also known as Bax inhibitor peptide P5); Kp7-6; FAIM(S) (Fas apoptosis inhibitory molecule-short); FAIM(L) (Fas apoptosis inhibitory molecule-long); Fas:Fc; FAP-1; NOK2; F2051; F1926; F2928; ZB4; Fas M3 mAb; EGF; 740 Y-P; SC 3036 (KKHTDDGYMPM-SPGVA) (SEQ ID NO:33); PI 3-kinase Activator (Santa Cruz Biotechnology, Inc.); $Pam_3Cys$ ((S)-(2,3-bis(palmitoyloxy)-(2RS)-propyl)-N-palmitoyl-(R)-Cys-(S)-Ser(S)-Lys-4-OH, trihydrochloride); Act1 (NT-kB activator 1); an anti-IkB antibody; Acetyl-11-keto-b-Boswellic Acid; Andrographolide; Caffeic Acid Phenethyl Ester (CAPE); Gliotoxin; Isohelenin; NEMO-Binding Domain Binding Peptide (DRQIKIWFQN-RRMKWKKTALDWSWLQTE) (SEQ ID NO: 34; NF-kB Activation Inhibitor (6-Amino-4-(4-phenoxyphenylethylamino)quinazoline); NF-kB Activation Inhibitor II (4-Methyl-N1-(3-phenylpropyl)benzene-1,2-diamine); NF-kB Activation Inhibitor III (3-Chloro-4-nitro-N-(5-nitro-2-thiazolyl)-benzamide); NF-kB Activation Inhibitor IV ((E)-2-Fluoro-4'-methoxystilbene); NF-kB Activation Inhibitor V (5-Hydroxy-(2,6-diisopropylphenyl)-1H-isoindole-1,3-dione); NF-kB SN50 (AAVALLPAVLLAL-LAPVQRKRQKLMP) (SEQ ID NO:35); Oridonin; Parthenolide; PPM-18 (2-Benzoylamino-1,4-naphthoquinone); Ro106-9920; Sulfasalazine; TIRAP Inhibitor Peptide (RQIKIWFNRRMKWKKLQLRDAAPGGAIVS) (SEQ ID NO:36); Withaferin A; Wogonin; BAY 11-7082 ((E)3-[(4-Methylphenyl)sulfonyl]-2-propenenitrile); BAY 11-7085 ((E)3-[(4-t-Butylphenyl)sulfonyl]-2-propenenitrile); (E)-Capsaicin; Aurothiomalate (ATM or AuTM); Evodiamine; Hypoestoxide; IKK Inhibitor III (BMS-345541); IKK Inhibitor VII; IKK Inhibitor X; IKK Inhibitor II; IKK-2 Inhibitor IV; IKK-2 Inhibitor V; IKK-2 Inhibitor VI; IKK-2 Inhibitor (SC-514); IkB Kinase Inhibitor Peptide; IKK-3 Inhibitor IX; ARRY-797 (Array BioPharma); SB-220025 (5-(2-Amino-4-pyrimidinyl)-4-(4-fluorophenyl)-1-(4-piperidinlyl)imidazole); SB-239063 (trans-4-[4-(4-Fluorophenyl)-5-(2-methoxy-4-pyrimidinyl)-1H-imidazol-1-yl]cyclohexanol); SB-202190 (4-(4-Fluorophenyl)-2-(4-hydroxyphenyl)-5-(4-pyridyl)1H-imidazole); JX-401 (-[2-Methoxy-4-(methylthio)benzoyl]-4-(phenylmethyl)piperidine); PD-169316 (4-(4-Fluorophenyl)-2-(4-nitrophenyl)-5-(4-pyridyl)-1H-imidazole); SKF-86002 (6-(4-Fluorophenyl)-2,3-dihydro-5-(4-pyridinyl)imidazo[2,1-b]thiazole dihydrochloride); SB-200646 (N-(1-Methyl-1H-indol-5-yl)-N'-3-pyridinylurea); CMPD-1 (2'-Fluoro-N-(4-hydroxyphenyl)-[1,1'-biphenyl]-4-butanamide); EO-1428 ((2-Methylphenyl)-[4-[(2-amino-4-bromophenyl)amino]-2-chlorophenyl]methanone); SB-253080 (4-[5-(4-Fluorophenyl)-2-[4-(methylsulfonyl)phenyl]-1H-imidazol-4-yl]pyridine); SD-169 (1H-Indole-5-carboxamide); SB-203580 (4-(4-Fluorophenyl)-2-(4-methylsulfinyl phenyl)-5-(4-pyridyl) 1H-imidazole); TZP-101 (Tranzyme Pharma); TZP-102 (Tranzyme Pharma); GHRP-6 (growth hormone-releasing peptide-6); GHRP-2 (growth hormone-releasing peptide-2); EX-1314 (Elixir Pharmaceuticals); MK-677 (Merck); L-692,429 (Butanamide, 3-amino-3-methyl-N-(2,3,4,5-tetrahydro-2-oxo-1-((2'-(1H-tetrazol-5-yl)(1,1'-biphenyl)-4-yl)methyl)-1H-1-benzazepin-3-yl)-, (R)—); EP1572 (Aib-DTrp-DgTrp-CHO); diltiazem; metabolites of diltiazem; BRE (Brain and Reproductive organ-Expressed protein); verapamil; nimodipine; diltiazem; omega-conotoxin; GVIA; amlodipine; felodipine; lacidipine; mibefradil; NPPB (5-Nitro-2-(3-phenylpropylamino)benzoic Acid); flunarizine; erythropoietin; piperine; hemin; brazilin; z-VAD-FMK (Benzyloxycarbonyl-Val-Ala-Asp (OMe)-fluoromethyl ketone fluoromethyl ketone); z-LEHD-FMK (benzyloxycarbonyl-Leu-Glu(OMe)-His-Asp(OMe)-fluoromethyl ketone) (SEQ ID NO:37): B-D-FMK (boc-aspartyl(OMe)-fluoromethyl ketone); Ac-LEHD-CHO (N-acetyl-Leu-Glu-His-Asp-CHO) (SEQ ID NO:38); Ac-IETD-CHO (N-acetyl-Ile-Glu-Thr-Asp-CHO) (SEQ ID NO:39); z-IETD-FMK (benzyloxycarbonyl-Ile-Glu(OMe)-Thr-Asp(OMe)-fluoromethyl ketone) (SEQ ID NO:40); FAM-LEHD-FMK (benzyloxycarbonyl Leu-Glu-His-Asp-fluoromethyl ketone) (SEQ ID NO:41); FAM-LETD-FMK (benzyloxycarbonyl Leu-Glu-Thr-Asp-fluoromethyl ketone) (SEQ ID NO:42); Q-VD-OPH (Quinoline-Val-Asp-CH$_2$—O-Ph); XIAP; cIAP-1; cIAP-2; ML-IAP; ILP-2; NAIP; Survivin; Bruce; IAPL-3; fortilin; leupeptine; PD-150606 (3-(4-Iodophenyl)-2-mercapto-(Z)-2-propenoic acid); MDL-28170 (Z-Val-Phe-CHO); calpeptin; acetyl-calpastatin; MG 132 (N-[(phenylmethoxy)carbonyl]-L-leucyl-N-[(1S)-1-formyl-3-methylbutyl]-L-leucinamide); MYODUR; BN 82270 (Ipsen); BN 2204 (Ipsen); AHLi-11 (Quark Pharmaceuticals), an mdm2 protein, (1-(4-Methylphenyl)-2-(4,5,6,7-tetrahydro-2-imino-3(2H)-benzothiazolyl)ethanone); trans-stilbene; cis-stilbene; resveratrol; piceatannol; rhapontin; deoxyrhapontin; butein; chalcon; isoliquirtigen; butein; 4,2',4'-trihydroxychalcone; 3,4,2',4',6'-pentahydroxychalcone; flavone; morin; fisetin; luteolin; quercetin; kaempferol; apigenin; gossypetin; myricetin; 6-hydroxyapigenin; 5-hydroxyflavone; 5,7,3',4',5'-pentahydroxyflavone; 3,7,3',4',5'-pentahydroxyflavone; 3,6,3',4'-tetrahydroxyflavone; 7,3',4',5'-tetrahydroxyflavone; 3,6,2',4'-tetrahydroxyflavone; 7,4'-dihydroxyflavone; 7,8,3',4'-tetrahydroxyflavone; 3,6,2',3'-tetrahydroxyflavone; 41-hydroxyflavone; 5-hydroxyflavone; 5,4'-dihydroxyflavone; 5,7-dihydroxyflavone; daidzein; genistein; naringenin; flavanone; 3,5,7,3',4'-pentahydroxyflavanone; pelargonidin chloride; cyanidin chloride; delphinidin chloride; (−)-epicatechin (Hydroxy Sites: 3,5,7,3',4'); (−)-catechin (Hydroxy Sites: 3,5,7,3',4'); (−)-gallocatechin (Hydroxy Sites: 3,5,7,3',4',5') (+)-catechin (Hydroxy Sites: 3,5,7,3',4'); (+)-epicatechin (Hydroxy Sites: 3,5,7,3,4); Hinokitiol (b-Thujaplicin; 2-hydroxy-4-isopropyl-2,4,6-cycloheptatrien-1-one); L-(+)-Ergothioneine ((S)-a-Carboxy-2,3-dihydro-N,N,N-trimethyl-2-thioxo-1H-imidazole-4-ethanaminium inner salt); Caffeic Acid Phenyl Ester; MCI-186 (3-Methyl-1-phenyl-2-pyrazolin-5-one); HBED (N,N'-Di-(2-hydroxybenzyl)ethylenediamine-N,N'-diacetic acide.H2O); Ambroxol (trans-4-(2-Amino-3,5-dibromobenzylamino)cyclohexane-HCl; and U-83836E ((−)-2-((4-(2,6-di-1-Pyrrolidinyl-4-pyrimidinyl)-1-piperazinyl)methyl)-3,4-dihydro-2,5,7,8-tetramethyl-2H-1-benzopyran-6-ol.2HCl); β-1'-5-methyl-nicotinamide-2'-deoxyribose; β-D-1'-5-methyl-nico-tinamide-2'-deoxyribofuranoside; β-1'-4,5-dimethyl-nicotinamide-2'-de-oxyribose; β-D-1'-4,5-dimethyl-nicotinamide-2'-deoxyribofuranoside; 1-Naphthyl PP1 (1-(1,1-Dimethylethyl)-3-(1-naphthalenyl)-1H-pyrazolo[3,4-d]pyrimidin-4-amine); Lavendustin A (5-[[(2,5-Dihydroxyphenyl)methyl][(2-hydroxyphenyl)methyl]amino]-2-hydroxybenzoic acid); MNS (3,4-Methylenedioxy-b-nitrostyrene); PP1 (1-(1,1-Dimethylethyl)-1-(4-methylphenyl)-1H-pyrazolo[3,4-d]pyrimidin-4-amine); PP2 (3-(4-chlorophenyl) 1-(1,1-dimethylethyl)-1H-pyrazolo[3,4-d]pyrimidin-4-amine); KX1-004 (Kinex); KX1-005 (Kinex); KX1-136 (Kinex); KX1-174 (Kinex); KX1-141 (Kinex); KX2-328 (Kinex); KX1-306 (Kinex); KX1-329 (Kinex); KX2-391 (Kinex); KX2-377 (Kinex); ZD4190 (Astra Zeneca; N-(4-bromo-2-fluorophenyl)-6-methoxy-7-(2-(1H-1,2,3-triazol-1-yl)ethoxy)quinazolin-4-amine); AP22408 (Ariad Pharmaceuticals); AP23236 (Ariad Pharmaceuticals); AP23451 (Ariad Pharmaceuticals); AP23464 (Ariad Pharmaceuticals); AZD0530 (Astra Zeneca); AZM475271 (M475271; Astra Zeneca); Dasatinib (N-(2-chloro-6-methylphenyl)-2-(6-(4-(2-hydroxyethyl)-piperazin-1-yl)-2-methylpyrimidin-4-ylamino)thiazole-5-carboxamide); GN963 (trans-4-(6,7-dimethoxyquinoxalin-2-ylamino)cyclohexanol sulfate); Bosutinib (4-((2,4-dichloro-5-methoxyphenyl)amino)-6-methoxy-7-(3-(4-methyl-1-piperazinyl)propoxy)-3-quinolinecarbonitrile); or combinations thereof.

Fluorescent Moieties

In some embodiments, the targeting molecule further comprises a fluorescent moiety (e.g., a fluorescent protein, peptide, or fluorescent dye molecule). All fluorescent moieties are encompassed within the term "fluorescent moiety." Specific examples of fluorescent moieties given herein, are illustrative and are not meant to limit the fluorescent moieties for use with the targeting molecules disclosed herein.

In some embodiments, the peptide or aptamer is directly bound to a fluorescent moiety. In some embodiments, the peptide or aptamer is indirectly (e.g., via a linker) bound to a fluorescent moiety. In some embodiments, two or more peptides or aptamers are directly or indirectly bound to a single fluorescent moiety.

Examples of fluorescent dyes include, but are not limited to, xanthenes (e.g., rhodamines, rhodols and fluoresceins, and their derivatives); bimanes; coumarins and their derivatives (e.g., umbelliferone and aminomethyl coumarins); aromatic amines (e.g., dansyl; squarate dyes); benzofurans; fluorescent cyanines; carbazoles; dicyanomethylene pyranes; polymethine; oxabenzanthrane; xanthene; pyrylium; carbostyl; perylene; acridone; quinacridone; rubrene; anthracene; coronene; phenanthrecene; pyrene; butadiene; stilbene; porphyrin; pthalocyanine; lanthanide metal chelate complexes; rare-earth metal chelate complexes; and derivatives of such dyes.

In some embodiments, the fluorescent moiety is a fluorescein dye. Examples of fluorescein dyes include, but are not limited to, 5-carboxyfluorescein, fluorescein-5-isothiocyanate and 6-carboxyfluorescein.

In some embodiments, the fluorescent moiety is a rhodamine dye. Examples of rhodamine dyes include, but are not limited to, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride (sold under the tradename of TEXAS RED®).

In some embodiments, the fluorescent moiety is a cyanine dye. Examples of cyanine dyes include, but are not limited to, Cy3, Cy3B, Cy3.5, Cy5, Cy5.5, Cy 7.

In some embodiments, the fluorescent moiety is a peptide. In some embodiments, the fluorescent moiety is Green Fluorescent Protein (GFP). In some embodiments, the fluorescent moiety is a derivative of GFP (e.g., EBFP, EBFP2, Azurite, mKalama1, ECFP, Cerulean, CyPet, YFP, Citrine, Venus, YPet).

Fluorescent labels are detected by any suitable method. For example, a fluorescent label may be detected by exciting the fluorochrome with the appropriate wavelength of light and detecting the resulting fluorescence, e.g., by microscopy, visual inspection, via photographic film, by the use of electronic detectors such as charge coupled devices (CCDs), photomultipliers, etc.

In some embodiments, the fluorescent moiety is conjugated to high molecular weight molecule, such as water soluble polymers including, but not limited to, dextran, PEG, serum albumin, or poly(amidoamine) dendrimer.

Linkers

In some embodiments, a cargo (e.g., a fluorescent moiety or drug) is directly attached to the targeting molecule, e.g. at the end of the targeting peptide. Alternatively, in some embodiments, a cargo (e.g., a fluorescent moiety or drug) is indirectly attached to a targeting molecule disclosed herein (e.g., via a linker).

As used herein, a "linker" is any molecule capable of binding (e.g., covalently) to a targeting molecule disclosed herein. Linkers include, but are not limited to, straight or branched-chain carbon linkers, heterocyclic carbon linkers, peptide linkers, and polyether linkers. For example, poly (ethylene glycol) linkers are available from Quanta Biodesign, Powell, Ohio. These linkers optionally have amide linkages, sulfhydryl linkages, or hetero functional linkages.

In some embodiments, the linker binds to a targeting molecule disclosed herein by a covalent linkage. In some embodiments, the covalent linkage comprises an ether bond, thioether bond, amine bond, amide bond, carbon-carbon bond, carbon-nitrogen bond, carbon-oxygen bond, or carbon-sulfur bond.

In some embodiments, the linker is flexible. In some embodiments, the linker is rigid.

In some embodiments, the linker comprises a linear structure. In some embodiments, the linker comprises a non-linear structure. In some embodiments, the linker comprises a branched structure. In some embodiments, the linker comprises a cyclic structure.

In some embodiments, the linker is an alkyl. In some embodiments, the linker is heteroalkyl.

In some embodiments, the linker is an alkylene. In some embodiments, the linker is an alkenylene. In some embodiments, the linker is an alkynylene. In some embodiments, the linker is a heteroalkylene.

An "alkyl" group refers to an aliphatic hydrocarbon group. The alkyl moiety may be a saturated alkyl or an unsaturated alkyl. Depending on the structure, an alkyl group can be a monoradical or a diradical (i.e., an alkylene group).

The "alkyl" moiety may have 1 to 10 carbon atoms (whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated). The alkyl group could also be a "lower alkyl" having 1 to 6 carbon atoms. The alkyl group of the compounds described herein may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from: methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, ethenyl, propenyl, butenyl, and the like.

In some embodiments, the linker comprises a ring structure (e.g., an aryl). As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be optionally substituted. Rings can be monocyclic or polycyclic.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

The term "cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyl groups include groups having from 3 to 10 ring atoms. Cycloalkyls include, but are not limited to, cyclopropyl, cyclobutyl, cyclopentyl, cyclohexyl, cycloheptyl, and cyclooctyl.

In some embodiments, the ring is a cycloalkane. In some embodiments, the ring is a cycloalkene.

In some embodiments, the ring is an aromatic ring. The term "aromatic" refers to a planar ring having a delocalized n-electron system containing 4n+2 it electrons, where n is an integer. Aromatic rings can be formed from five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

In some embodiments, the ring is a heterocycle. The term "heterocycle" refers to heteroaromatic and heteroalicyclic groups containing one to four heteroatoms each selected from O, S and N, wherein each heterocyclic group has from 4 to 10 atoms in its ring system, and with the proviso that the ring of said group does not contain two adjacent O or S atoms. Non-aromatic heterocyclic groups include groups having only 3 atoms in their ring system, but aromatic heterocyclic groups must have at least 5 atoms in their ring system. The heterocyclic groups include benzo-fused ring systems. An example of a 3-membered heterocyclic group is aziridinyl. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems and ring systems substituted with one or two oxo (=O) moieties such as pyrrolidin-2-one. Depending on the structure, a heterocycle group can be a monoradical or a diradical (i.e., a heterocyclene group).

In some embodiments, the ring is fused. The term "fused" refers to structures in which two or more rings share one or more bonds. In some embodiments, the ring is a dimer. In some embodiments, the ring is a trimer. In some embodiments, the ring is a substituted.

The term "carbocyclic" or "carbocycle" refers to a ring wherein each of the atoms forming the ring is a carbon atom. Carbocycle includes aryl and cycloalkyl. The term thus distinguishes carbocycle from heterocycle ("heterocyclic") in which the ring backbone contains at least one atom which is different from carbon (i.e., a heteroatom). Heterocycle includes heteroaryl and heterocycloalkyl. Carbocycles and heterocycles can be optionally substituted.

In some embodiments, the linker is substituted. The teen "optionally substituted" or "substituted" means that the referenced group may be substituted with one or more additional group(s) individually and independently selected from $C_1$-$C_6$alkyl, $C_3$-$C_8$cycloalkyl, aryl, heteroaryl, $C_2$-$C_6$heteroalicyclic, hydroxy, $C_1$-$C_6$alkoxy, aryloxy, $C_1$-$C_6$alkylthio, arylthio, $C_1$-$C_6$alkylsulfoxide, arylsulfoxide, $C_1$-$C_6$alkylsulfone, arylsulfone, cyano, halo, $C_2$-$C_8$acyl, $C_2$-$C_8$acyloxy, nitro, $C_1$-$C_6$haloalkyl, $C_1$-$C_6$fluoroalkyl, and amino, including $C_1$-$C_6$alkylamino, and the protected derivatives thereof. By way of example, an optional substituents may be $L^sR^s$, wherein each $L^s$ is independently selected from a bond, —O—, —C(=O)—, —S—, —S(=O)—, —S(=O)$_2$—, —NH—, —NHC(=O)—, —C(=O)N—, S(=O)$_2$NH—, —NHS(=O)$_2$—, —OC(=O)NH—, —NHC(=O)O—, —($C_1$-$C_6$alkyl)-, or —($C_2$-$C_6$alkenyl)-; and each $R^s$ is independently selected from H, ($C_1$-$C_4$alkyl), ($C_3$-$C_8$cycloalkyl), heteroaryl, aryl, and $C_1$-$C_6$heteroalkyl. Optionally substituted non-aromatic groups may be substituted with one or more oxo (=O). The protecting groups that may form the protective derivatives of the above substituents are known to those of skill in the art.

In some embodiments, a bifunctional linker having one functional group reactive with a group on one molecule (e.g., a targeting molecule), and another group reactive on the other molecule (e.g., a fluorescent moiety or a drug), is used to form the desired conjugate. Alternatively, in some embodiments, derivatization is performed to provide functional groups. Thus, for example, procedures for the generation of free sulfhydryl groups on peptides are also known (See U.S. Pat. No. 4,659,839). A linker may alternatively comprise a heterobifunctional crosslinker comprising two or more different reactive groups that form a heterocyclic ring that can interact with a targeting molecule. For example, a heterobifunctional crosslinker such as cysteine may comprise an amine reactive group and a thiol-reactive group can interact with an aldehyde on a derivatized targeting molecule. Additional combinations of reactive groups suitable for heterobifunctional crosslinkers include, for example, amine- and sulfhydryl reactive groups; carbonyl and sulfhydryl reactive groups; amine and photoreactive groups; sulfhydryl and photoreactive groups; carbonyl and photoreactive groups; carboxylate and photoreactive groups; and arginine and photoreactive groups.

In some embodiments, a peptide linker consisting of one or more amino acids is used to join the targeting molecule and a fluorescent moiety or drug. Generally the peptide linker will have no specific biological activity other than to join the molecules or to preserve some minimum distance or other spatial relationship between them. However, the constituent amino acids of the linker may be selected to influence some property of the molecule such as the folding, net charge, or hydrophobicity. In some embodiments the peptide linker is relatively short, typically less than about 10 amino acids, preferably less than about 8 amino acids and more preferably less than 5 amino acids. Non-limiting illustrative examples include glycine and glycine-serine linkers which can be added to the C-terminus of a targeting peptide.

Further Modifications

In some embodiments, the targeting molecules of the present invention are optionally conjugated to high molecular weight molecules that increase the multivalency and avidity of labeling. In some embodiments, the high molecular weight molecules are water-soluble polymers. Examples of suitable water-soluble polymers include, but are not limited to, peptides, saccharides, poly(vinyls), poly(ethers), poly(amines), poly(carboxylic acids) and the like. In some embodiments, the water-soluble polymers is dextran, polyethylene glycol (PEG), polyoxyalkylene, polysialic acid, starch, or hydroxyethyl starch. Any suitable method is used to conjugate peptides to water-soluble polymers (see Heimanson G., *Bioconjugate Techniques* 2$^{nd}$ *Ed.*, Academic Press, Inc. 2008).

In some embodiments, the targeting molecules of the present invention are conjugated to factors having neurotrophic properties (e.g., neurotrophic proteins such as nerve growth factor (NGF), brain-derived neurotrophic factor (BDNF), neurotrophin-3 (NT-3), neurotrophin-4 (NT-4), glial cell line-derived neurotrophic factor (GDNF), ciliary neurotrophic factor (CNTF) as well as non-protein small molecules with neurotrophic properties).

Methods
Labeling

Disclosed herein, in certain embodiments, are methods of labeling a neuron or nerve (or component of either) by contacting a neuron or nerve with a targeting molecule described.

In some embodiments, the contacting occurs in vivo. In some embodiments, the contacting occurs in vitro.

In some embodiments, a neuron or nerve (or component thereof) is labeled for identification during surgery. In some embodiments, the method comprises administering a targeting molecule disclosed herein to a subject that will undergo surgery. In some embodiments, the method comprises administering a targeting molecule disclosed herein to a subject that is undergoing surgery. In some embodiments, a targeting molecule disclosed herein is administered to a patient systemically. In some embodiments, a targeting molecule disclosed herein is administered to a patient locally.

Drug Delivery

Disclosed herein, in certain embodiments, are methods of targeted drug delivery. In some embodiments, a targeting molecule disclosed herein delivers a drug to a specific target. In some embodiments, a targeting molecule disclosed herein delivers a drug to a neuron or nerve.

In some embodiments, the drug is an agent that reduces pain (either the perception of pain or activity of a painful stimulant). In some embodiments, the drug is an anesthetic. In some embodiments, the drug is benzocaine; carticaine; cinchocaine; cyclomethycaine; lidocaine; prilocaine; propxycaine; proparacaine; tetracaine; tocainide; and trimecaine; or a combination thereof.

In some embodiments, the drug is an agent that modulates death (e.g., via apoptosis or necrosis) of a neuron or nerve. In some embodiments, the drug is a cytotoxic agent. In some embodiments, the drug is methotrexate (RHEUMATREX®, Amethopterin); cyclophosphamide (CYTOXAN®); thalidomide (THALIDOMID®); paclitaxel; pemetrexed; pentostatin; pipobroman; pixantrone; plicamycin; procarbazine; proteasome inhibitors (e.g.; bortezomib); raltitrexed; rebeccamycin; rubitecan; SN-38; salinosporamide A; satraplatin; streptozotocin; swainsonine; tariquidar; taxane; tegafur-uracil; temozolomide; testolactone; thioTEPA; tioguanine; topotecan; trabectedin; tretinoin; triplatin tetranitrate; tris(2-chloroethyl)amine; troxacitabine; uracil mustard; valrubicin; vinblastine; vincristine; vinorelbine; vorinostat; zosuquidar; or a combination thereof. In some embodiments, the drug is a pro-apoptotic agent. In some embodiments, the drug is an anti-apoptotic agent. In some embodiments, the drug is selected from: minocycline; SB-203580 (4-(4-Fluorophenyl)-2-(4-methylsulfinyl phenyl)-5-(4-pyridyl)1H-imidazole); PD 169316 (4-(4-Fluorophenyl)-2-(4-nitrophenyl)-5-(4-pyrid)-1H-imidazole); SB 202190 (4-(4-Fluorophenyl)-2-(4-hydroxyphenyl)-5-(4-pyridyl)1H-imidazole); RWJ 67657 (4-[4-(4-fluorophenyl)-1-(3-phenylpropyl)-5-(4-pyridinyl)-1H-imidazol-2-yl]-3-butyn-1-ol); SB 220025 (5-(2-Amino-4-pyrimidinyl)-4-(4-fluorophenyl)-1-(4-piperidinlyl)imidazole); D-JNKI-1 ((D)-hJIP$_{175\text{-}157}$-DPro-DPro-(D)-HIV-TAT$_{57\text{-}48}$); AM-111 (Auris); SP600125 (anthra[1,9-cd]pyrazol-6(2H)-one); JNK Inhibitor I ((L)-HIV-TAT$_{48\text{-}57}$-PP-JBD$_{20}$); JNK inhibitor III ((L)-HIV-TAT$_{47\text{-}57}$-gaba-c-Jun$\delta_{33\text{-}57}$); AS601245 (1,3-benzothiazol-2-yl (2-[[2-(3-pyridinyl)ethyl]amino]-4 pyrimidinyl)acetonitrile); JNK Inhibitor VI (H$_2$N-RPKRPTTLNLF-NH$_2$) (SEQ ID NO:32); JNK Inhibitor VIII (N-(4-Amino-5-cyano-6-cthoxypyridin-2-yl)-2-(2,5-dimethoxyphenyl)acetamide); JNK Inhibitor IX (N-(3-Cyano-4,5,6,7-tetrahydro-1-benzothien-2-yl)-1-naphthamide); dicumarol (3,3'-Methylenebis(4-hydroxycoumarin)); SC-236 (4-[5-(4-chlorophenyl)-3-(trifluoromethyl)-1H-pyrazol-1-yl]benzene-sulfonamide); CEP-1347 (Cephalon); CEP-11004 (Cephalon); an artificial protein comprising at least a portion of a Bcl-2 polypeptide; a recombinant FNK; V5 (also known as Bax inhibitor peptide V5); Bax channel blocker ((±)-1-(3,6-Dibromocarbazol-9-yl)-3-piperazin-1-yl-propan-2-ol); Bax inhibiting peptide P5 (also known as Bax inhibitor peptide P5); Kp7-6; FAIM(S) (Fas apoptosis inhibitory molecule-short); FAIM(L) (Fas apoptosis inhibitory molecule-long); Fas:Fc; FAP-1; NOK2; F2051; F1926; F2928; ZB4; Fas M3 mAb; EGF; 740 Y-P; SC 3036 (KKHTDDGYMPMSPGVA) (SEQ ID NO:43); PI 3-kinase Activator (Santa Cruz Biotechnology, Inc.); Pam$_3$Cys ((S)-(2,3-bis(palmitoyloxy)-(2RS)-propyl)-N-palmitoyl-(R)-Cys-(S)-Ser(S)-Lys-4-OH, trihydrochloride); Act1 (NF-kB activator 1); an anti-IkB antibody; Acetyl-11-keto-b-Boswellic Acid; Andrographolide; Caffeic Acid Phenethyl Ester (CAPE); Gliotoxin; Isohelenin; NEMO-Binding Domain Binding Peptide (DRQIKIWFQNRRMKWKKTALD-WSWLQTE) (SEQ ID NO:34); NE-kB Activation Inhibitor (6-Amino-4-[(4-phenoxyphenylethylamino)quinazoline); NF-kB Activation Inhibitor II (4-Methyl-N1-(3-phenylpropyl)benzene-1,2-diamine); NF-kB Activation Inhibitor III (3-Chloro-4-nitro-N-(5-nitro-2-thiazolyl)-benzamide); NF-kB Activation Inhibitor IV ((E)-2-Fluoro-4'-methoxystilbene); NE-kB Activation Inhibitor V (5-Hydroxy-(2,6-diisopropylphenyl)-1H-isoindole-1,3-dione): NF-kB SN 50 (AAVALLPAVLLALLAPVQRKRQKLMP) (SEQ ID NO:35); Oridonin; Parthenolide; PPM-18 (2-Benzoylamino-1,4-naphthoquinone); Ro106-9920; Sulfasalazine; TIRAP Inhibitor Peptide (RQIKIWFNRRMKWKKLQLRDAAPG-GAIVS) (SEQ ID NO:36): Withaferin A; Wogonin; BAY 11-7082 ((E)3-[(4-Methylphenyl)sulfonyl]-2-propenenitrile); BAY 11-7085 ((E)3-[(4-t-Butylphenyl)sulfonyl]-2-propenenitrile); (E)-Capsaicin; Aurothiomalate (ATM or AuTM); Evodiamine; Hypoestoxide; IKK Inhibitor III (BMS-345541); IKK inhibitor VII; IKK Inhibitor X; IKK Inhibitor II; IKK-2 inhibitor IV; IKK-2 Inhibitor V; IKK-2 Inhibitor VI; IKK-2 Inhibitor (SC-514); IkB Kinase Inhibitor Peptide; IKK-3 Inhibitor IX; ARRY-797 (Array BioPharma); SB-220025 (5-(2-Amino-4-pyrimidinyl)-4-(4-fluorophenyl)-1-(4-piperidinlyl)imidazole); SB-239063 (trans-4-[4-(4-Fluorophenyl)-5-(2-methoxy-4-pyrimidinyl)-1H-imidazol-1-yl]cyclohexanol); SB-202190 (4-(4-Fluorophenyl)-2-(4-hydroxyphenyl)-5-(4-pyridyl)1H-imidazole); JX-401 (-[2-Methoxy-4-(methylthio)benzoyl]-4-(phenylmethyl)piperidine); PD-169316 (4-(4-Fluorophenyl)-2-(4-nitrophenyl)-5-(4-pyridyl)-1H-imidazole); SKF-86002 (6-(4-Fluorophenyl)-2,3-dihydro-5-(4-pyridinyl)imidazo[2,1-b] thiazole dihydrochloride); SB-200646 (N-(1-Methyl-1H-indol-5-yl)-N'-3-pyridinylurea); CMPD-1 (2'-Fluoro-N-(4-hydroxyphenyl)-[1,1'-biphenyl]-4-butanamide); EO-1428 ((2-Methylphenyl)-[4-[(2-amino-4-bromophenyl)amino]-2-chlorophenyl]methanone); SB-253080 (4-[5-(4-Fluorophenyl)-2-[4-(methylsulfonyl)phenyl]-1H-imidazol-4-yl]pyridine); SD-169 (1H-Indole-5-carboxamide); SB-203580 (4-(4-Fluorophenyl)-2-(4-methylsulfinyl phenyl)-5-(4-pyridyl)1H-imidazole); TZP-101 (Tranzyme Pharma); TZP-102 (Tranzyme Pharma); GHRP-6 (growth hormone-releasing peptide-6); GHRP-2 (growth hormone-releasing peptide-2); EX-1314 (Elixir Pharmaceuticals); MK-677 (Merck); L-692,429 (Butanamide, 3-amino-3-methyl-N-(2,3,4,5-tetrahydro-2-oxo-1-((2'-(1H-tetrazol-5-yl)(1,1'-biphenyl)-4-yl)methyl)-1H-1-benzazepin-3-yl)-, (R)—); EP1572 (Aib-DTrp-DgTrp-CHO); diltiazem; metabolites of diltiazem; BRE (Brain and Reproductive organ-Expressed protein); verapamil; nimodipine; diltiazem; omega-conotoxin; GVIA; amlodipine; felodipine; lacidipine; mibefradil; NPPB (5-Nitro-2-(3-phenylpropylamino)benzoic Acid); flunarizine; erythropoietin; piperine; hemin; brazilin; z-VAD-FMK (Benzyloxycarbonyl-Val-Ala-Asp(OMe)-fluoromethyl ketone); z-LEHD-FMK (benzyloxycarbonyl-Leu-Glu(OMe)-His-Asp(OMe)-fluoromethyl ketone) (SEQ ID NO:37); B-D-FMK (boc-aspartyl(OMe)-fluoromethyl ketone); Ac-LEHD-CHO (N-acetyl-Leu-Glu-His-Asp-CHO) (SEQ ID NO:38); Ac-LEHD-CHO Asp-CHO) (SEQ ID NO:39); z-IETD-FMK (benzyloxycarbonyl-Ile-Glu(OMe)-Thr-Asp(OMe)-fluoromethyl ketone) (SEQ ID NO:40); FAM-LEHD-FMK (benzyloxycarbonyl Leu-Glu-His-Asp-fluoromethyl ketone) (SEQ ID NO:41); FAM-LETD-FMK (benzyloxycarbonyl Leu-Glu-Thr-Asp-fluoromethyl ketone) (SEQ ID NO:42); Q-VD-OPH (Quinoline-Val-Asp-CH$_2$—O-Ph); XIAP; cIAP-1; cIAP-2; ML-IAP; ILP-2; NAIP; Survivin; Bruce; IAPL-3; fortilin; leupeptine; PD-150606 (3-(4-Iodophenyl)-2-mercapto-(Z)-2-propenoic acid); MDL-28170 (Z-Val-Phe-CHO); calpeptin; acetyl-calpastatin; MG 132 (N-[(phenylmethoxy)carbonyl]-L-leucyl-N-[(1S)-1-formyl-3-methylbutyl]-L-leucinamide); MYODUR; BN 82270 (Ipsen); BN 2204 (Ipsen); AHLi-11 (Quark Pharmaceuticals), an mdm2 protein, pifithrin-α (1-(4-Methylphenyl)-2-(4,5,6, tetrahydro-2-imino-3(2H)-benzothiazolyl)ethanone); trans-stilbene; cis-stilbene; resveratrol; piceatannol; rhapontin; deoxyrhapontin; butein; chalcon; isoliquirtigen; butein; 4,2',4'-trihydroxychalcone; 3,4,2',4',6'-pentahydroxychalcone; flavone; morin; fisetin; luteolin; quercetin; kaempferol; apigenin; gossypetin; myricetin; 6-hydroxyapigenin; 5-hydroxyflavone; 5,7,3',4',5'-pentahydroxyflavone; 3,7,3',4',5'-pentahydroxyflavone; 3,6,3',4'-tetrahydroxyflavone; 7,3',4',5'-tetrahydroxyflavone; 3,6,2',4'-tetrahydroxyflavone; 7,4'-dihydroxyflavone; 7,8,3',4'-tetrahydroxyflavone; 3,6,2',3'-tetrahydroxyflavone; 4'-hydroxyflavone; 5-hydroxyflavone; 5,4'-dihydroxyflavone; 5,7-dihydroxyflavone; daidzein; genistein; naringenin; flavanone; 3,5,7,3',4'-pentahydroxyflavanone; pelargonidin chloride; cyanidin chloride; delphinidin chloride; (−)-epicatechin (Hydroxy Sites: 3,5,7,3',4'); (−)-catechin (Hydroxy Sites: 3,5,7,3',4'); (−)-gallocatechin (Hydroxy Sites: 3,5,7,3',4',5') (+)-catechin (Hydroxy Sites: 3,5,7,3',4'); (+)-epicatechin (Hydroxy Sites: 3,5,7,3',4'); Hinokitiol (b-Thujaplicin; 2-hydroxy-4-isopropyl-2,4,6-cycloheptatrien-1-one); L-(+)-Ergothioneine ((S)-a-Carboxy-2,3-dihydro-N,N,N-trimethyl-2-thioxo-1H-imidazole-4-ethanaminium inner salt); Caffeic Acid Phenyl Ester; MCI-186 (3-Methyl-1-phenyl-2-pyrazolin-5-one); HBED (N,N'-Di-(2-hydroxybenzyl)ethylenediamine-N,N'-diacetic acid.H2O); Ambroxol (trans-4-(2-Amino-3,5-dibromobenzylamino)cyclohexane-HCl; and U-83836E ((−)-24 (4-(2,6-di-1-Pyrrolidinyl-4-pyrimidinyl)-1-piperazinyl) methyl)-3,4-dihydro-2,5,7,8-tetramethyl-2H-1-benzopyran-6-ol.2HCl); β-1'-5-methyl-nicotinamide-2'-deoxyribose; β-D-1'-5-methyl-nico-tinamide-2'-deoxyribofuranoside; β-1'-4,5-dimethyl-nicotinamide-2'-de-oxyribose; B-D-1'-4,5-dimethyl-nicotinamide-2'-deoxyribofuranoside; 1-Naphthyl PP1 (1-(1,1-Dimethylethyl)-3-(1-naphthalenyl)-1H-pyrazolo[3,4-d]pyrimidin-4-amine); Lavendustin A (5-[[(2,5-Dihydroxyphenyl)methyl][(2-hydroxyphenyl)methyl]amino]-2-hydroxybenzoic acid); MNS (3,4-Methylenedioxy-b-nitrostyrene); PP1 (1-(1,1-Dimethylethyl)-1-(4-methylphenyl)-1H-pyrazolo[3,4-d]pyrimidin-4-amine); PP2 (3-(4-chlorophenyl) 1-(1,1-dimethylethyl)-1H-pyrazolo[3,4-d]pyrimidin-4-amine); KX1-004 (Kinex); KX1-005 (Kinex); KX1-136 (Kinex); KX1-174 (Kinex); KX1-141 (Kinex); KX2-328 (Kinex); KX1-306 (Kinex); KX1-329 (Kinex); KX2-391 (Kinex); KX2-377 (Kinex); ZD4190 (Astra Zeneca; N-(4-bromo-2-fluorophenyl)-6-methoxy-7-(2-(1H-1,2,3-triazol-1-yl) ethoxy)quinazolin-4-amine); AP22408 (Ariad Pharmaceuticals); AP23236 (Ariad Pharmaceuticals); AP23451 (Ariad Pharmaceuticals); AP23464 (Ariad Pharmaceuticals); AZD0530 (Astra Zeneca); AZM475271 (M475271; Astra Zeneca); Dasatinib (N-(2-chloro-6-methylphenyl)-2-(6-(4-(2-hydroxyethyl)-piperazin-1-yl)-2-methylpyrimidin-4-ylamino)thiazole-5-carboxamide); GN963 (trans-4-(6,7-dimethoxyquinoxalin-2ylamino)cyclohexanol sulfate); Bosutinib (4-((2,4-dichloro-5-methoxyphenyl)amino)-6-methoxy-7-(3-(4-methyl-1-piperazinyl)propoxy)-3-quinolinecarbonitrile); or combinations thereof.

In some embodiments, the drug is an agent that reduces undesired neuron or nerve impulses. In some embodiments, the drug reduces one or more symptoms of dyskinesia or synkinesia. In some embodiments, the drug is carbamazepine, oxcarbazepine, phenytein, valproic acid, sodium valproate, cinnarizine, flunarizine, or nimodipine, or combinations thereof.

In some embodiments, the drug is an agent that promotes regeneration of neuron or nerve tissue. In some embodiments, the drug is a growth factor. In some embodiments, the drug is selected from: brain-derived neurotrophic factor (BDNF); ciliary neurotrophic factor (CNTF); glial cell-line derived neurotrophic factor (GDNF); neurotrophin-3; neurotrophin-4; fibroblast growth factor (FGF) receptor; insulin-like growth factor (IGF); or a combination thereof.

Pharmaceutical Compositions

Disclosed herein, in certain embodiments, are pharmaceutical compositions comprising a targeting molecule disclosed herein. Pharmaceutical compositions herein are formulated using one or more physiologically acceptable carriers including excipients and auxiliaries which facilitate processing of the active agents into preparations which are used pharmaceutically. Proper formulation is dependent upon the route of administration chosen. A summary of pharmaceutical compositions is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999).

In certain embodiments, a pharmaceutical composition disclosed herein further comprises a pharmaceutically acceptable diluent(s), excipient(s), or carrier(s). In some embodiments, the pharmaceutical compositions includes other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions also contain other therapeutically valuable substances.

In certain embodiments, a pharmaceutical composition disclosed herein is administered to a subject by any suitable administration route, including but not limited to, parenteral (intravenous, subcutaneous, intraperitoneal, intramuscular, intravascular, intrathecal, intravitreal, infusion, or local) administration.

Formulations suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity is maintained, for example, by the use of a coating such as lecithin, by the maintenance of the required particle size in the case of dispersions, and by the use of surfactants. Formulations suitable for subcutaneous injection also contain optional additives such as preserving, wetting, emulsifying, and dispensing agents.

For intravenous injections, an active agent is optionally formulated in aqueous solutions, preferably in physiologically compatible buffers such as Hank's solution, Ringer's solution, or physiological saline buffer.

Parenteral injections optionally involve bolus injection or continuous infusion. Formulations for injection are optionally presented in unit dosage form, e.g., in ampoules or in multi dose containers, with an added preservative. In some embodiments, the pharmaceutical composition described herein are in a form suitable for parenteral injection as a sterile suspensions, solutions or emulsions in oily or aqueous vehicles, and contain formulatory agents such as suspending, stabilizing and/or dispersing agents. Pharmaceutical formulations for parenteral administration include aqueous solutions of an active agent in water soluble form. Additionally, suspensions are optionally prepared as appropriate oily injection suspensions.

In some embodiments, the pharmaceutical composition described herein is in unit dosage forms suitable for single administration of precise dosages. In unit dosage form, the formulation is divided into unit doses containing appropriate quantities of an active agent disclosed herein. In some embodiments, the unit dosage is in the form of a package containing discrete quantities of the formulation. Non-limiting examples are packaged tablets or capsules, and powders in vials or ampoules. In some embodiments, aqueous suspension compositions are packaged in single-dose non-reclosable containers. Alternatively, multiple-dose reclosable containers are used, in which case it is typical to include a preservative in the composition. By way of example only, formulations for parenteral injection are presented in unit dosage form, which include, but are not limited to ampoules, or in multi dose containers, with an added preservative.

EXAMPLES

Example 1

Identification and Characterization of Peptides Having Nerve Binding Affinity

Identification of Peptides having Specific Nerve Affinity

Phage display screens were performed to identify peptides that bind myelinated nerves and therefore could be useful for systemic in vivo labeling of nerves during fluorescence assisted surgery. In vitro selection strategies were performed with either excised murine nerves or purified myelin basic protein (MBP), and an in vivo selection was performed by injecting the phage library into living mice and harvesting nerve tissue for phage isolation.

In the in vitro selection against MBP, after 5 binding and wash cycles, 80% of isolated phage represented a single phage with its variable sequence coding for the peptide TYTDWLNFWAWP (SEQ ID NO:2) (Table 1). Additional unique sequence that were isolated after 4-5 rounds of selection for binding to MBP were LTPLPLPTPKPP (SEQ ID NO:6), VSTMPMSNMNGP (SEQ ID NO:7), GIFERNFGAMLH (SEQ ID NO:8), ACLREYHNWC (SEQ ID NO:9), MHRQPIAPVSSL (SEQ ID NO:10), SFADPLLFLAPP (SEQ ID NO:11), ASAHHMFTPGFD (SEQ ID NO:12).

The in vitro selection against excised nerves yielded three sequences that were repeated. Of 14 specific phage sequences at the end of 7 rounds of selection, 5 coded for the peptide NTQTLAKAPEHT (SEQ ID NO:4), 3 for the peptide KSLSRHDHIHHH (SEQ ID NO:3), and 2 for the peptide DFTKTSPLGIH (SEQ ID NO:5), with the remaining phage sequences being represented only once (Table 1).

In two additional selections, phage populations from the late round selections for either binding to MBP or to in vitro nerve were used for a secondary selection using the alternative selection strategy. (i.e. phage populations selected for MBP were selected for nerve binding and phage populations selected for nerve binding phage were selected for binding to MBP. From this selection 8 additional unique sequences were identified in addition to the sequences identified previously. The sequences of these phages were:

VAPTKAPLHSPS, (SEQ ID NO: 13)

NNLKTGTSAPTG, (SEQ ID NO: 14)

HKTAQWPFIAFR, (SEQ ID NO: 15)

RLTNAPAYQAPA, (SEQ ID NO: 16)

MQNPLNGKPGR, (SEQ ID NO: 17)

THYSRSLTDGTR, (SEQ ID NO: 18)

FSTSNNQSSPAI, (SEQ ID NO: 19)

YPSPNRPPNLTN. (SEQ ID NO: 20)

The in vivo selection did not yield any duplicated phage after 8 rounds of selection, perhaps because fluid circulation around nerves in vivo may not be strong enough to discriminate specifically bound phage from mechanically trapped or accidentally lodged phage. However, one in vivo selected sequence, AHHNSWKAKHHS (SEQ NO:1), was chosen for further testing (peptide synthesis and conjugation) because it contained multiple histidines reminiscent of the sequence KSLSRHDHIHHH (SEQ ID NO:3) from the in vitro selection against excised nerves (Table 1). Additional unique sequences identified using this in vivo selection were: DIANPPPPPLYV (SEQ ID NO:21), ALQTDGPFAESA (SEQ ID NO:22), DNAQHSERFPVP (SEQ ID NO:23), IPPTFPDRIRAPG (SEQ ID NO:24).

TABLE 1

Peptides selected from phage display screen

| Selection strategy | Peptide sequence | Name |
|---|---|---|
| In vivo | AHHNSWKAKHHS | SEQ ID NO: 1 |
| In vitro against MBP | TYTDWLNFWAWP | SEQ ID NO: 2 |
| In vitro against excised nerves | KSLSRHDHIHHH | SEQ ID NO: 3 |
| | NTQTLAKAPEHT | SEQ ID NO: 4 |
| | DFTKTSPLGIH | SEQ ID NO: 5 |
| Control random sequence | STARDLWPHGKE | SEQ ID NO: 44 |

Phage selected sequences were resynthesized as peptides for in vitro and in vivo testing. For the initial synthesis of these peptides, several amino acids were added to preserve the context of which sequences were screened on phage and to add a flexible linker between the peptide and dye. Specifically, at the N-terminus SHS contained within the phage linker was added to conserve some of the context in which the peptides were screened as fusion proteins on the phage surface. In addition, a C-terminus glycine was included to provide a flexible linker between the dye and the peptide. Removal of these residues could result in either an increase or decrease in nerve binding. A control sequence STARDLW-PHGKE (SEQ ID NO:44) was designed to be similar to the sequences that were made into peptides, although in a scrambled order.

To test the nerve binding affinity of each of the isolated peptide sequences in vitro, dissected nerve tissue was removed from mice and incubated for one hour with 100 nM of each peptide, including a control peptide made up of amino acids that were contained within the various phages selected and sequenced, but in a mixed-up order and designed without repeating any single amino acid except for glycine (which was added to the C-terminus as a flexible linker). Peptide with sequence TYTDWLNFWAWP (designated as SEQ ID NO:2) showed about little increase in uptake compared to no peptide or control peptide. We did detect a 10-fold increase in binding of this peptide to MBP crosslinked beads compared to control beads (with no MBP) confirming specific binding of TYTD-WLNFWAWP (SEQ ID NO:2) to MBP. For the remaining peptides AHHNSWKAKHHS (SEQ ID NO:1), KSLSRH-DHIHHH (SEQ ID NO:3), NTQTLAKAPEHT (SEQ ID NO:4), and DFTKTSPLGIH (SEQ ID NO:5), binding ranged from a two-fold increase over control to no difference from control.

Figure 2:
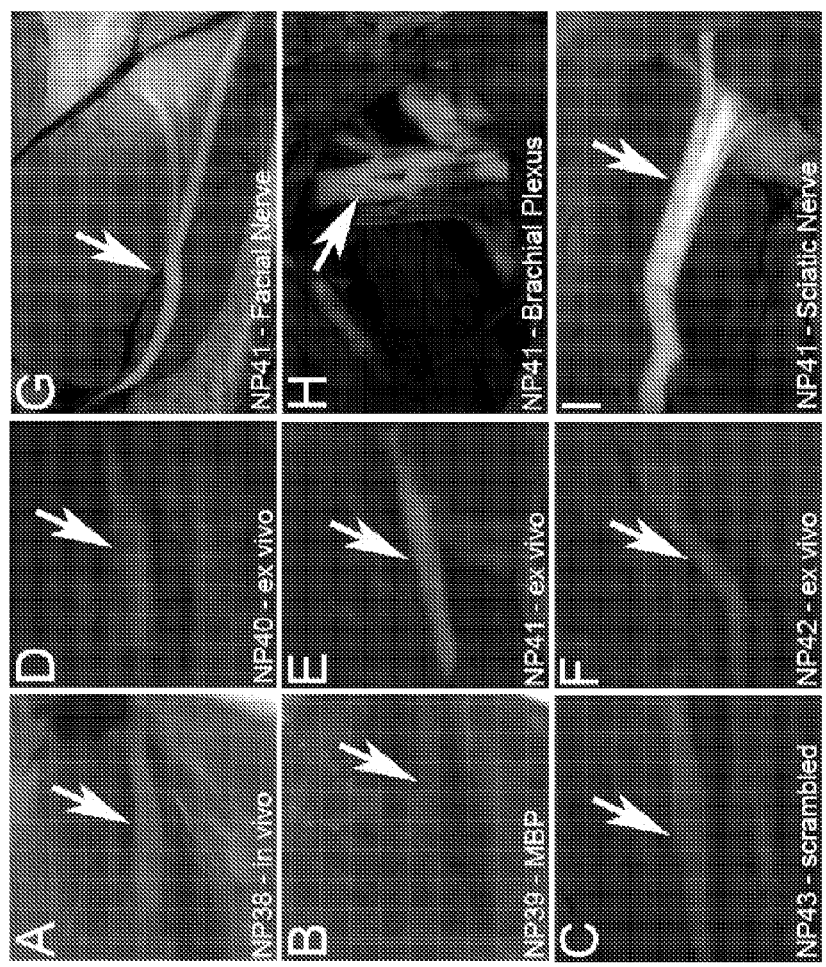
FIG. 2. Nerve binding affinity of FAM-labeled peptides. A-F. Fluorescence images of exposed sciatic nerves in living mice following administration of (A) acetyl-SHSAHHNSWKAKHHSGK(5,6FAM)-amide (SEQ ID NO:27); (B) acetyl-SHSTYTDWLNFWAWPGK(5,6FAM)-amide (SEQ ID NO:28); (C) SEQ ID NO:26; (D) acetyl-SHSKSLSRHDHIHHHGK(5,6FAM)-amide (SEQ ID NO:29); (E) SEQ ID NO:25; and (F) acetyl-SHSDFT-KTSPLGIHGK(5,6FAM)-amide (SEQ ID NO:30), G-I. Systemic survey of nerves labeled in animals injected with SEQ ID NO:25, including (G) facial nerve; (H) brachial plexus; and (I) sciatic nerve.

To test the nerve binding affinity of each of the isolated peptide sequences in vivo, carboxyfluorescein (FAM)-labeled peptides were injected intravenously into living mice. Following a wash-out period, the contrast between nerve and muscle binding of the labeled peptides was evaluated. FIG. 1 shows fluorescence images of exposed sciatic nerves in living mice injected with (SEQ ID NO:25) as compared to the control SEQ ID NO:26. In SEQ ID NO:4-labeled mice (FIGS. 1A-1B), the nerves show a 4-fold higher fluorescence than adjacent non-neural tissue, while NP43-labeled mice (FIG. 1C) show a 2-fold increase in fluorescence in nerves; the low level of labeling in NP43 control mice is likely due, at least in part, to the nonspecific binding of the fluorescein fluorophore to a variety of tissues. For the sequence identified through the in vivo selection (SEQ ID NO:1, FIG. 2A) and the sequence identified through in vitro selection against MBP (SEQ ID NO:2, FIG. 2B), little significant nerve-to muscle contrast was observed, as both peptides yielded high background binding to the surrounding non-neural tissue, similar to that of the control scrambled sequence (NP43, FIG. 2C). The peptide sequence with the best nerve to non-nerve contrast was SEQ ID NO:4, the sequence identified through the in vitro selection against excised nerves with the highest repeats (FIG. 2E). The other two sequences identified through this same selection strategy (SEQ ID NO:3 and SEQ ID NO:5) also exhibited nerve to muscle contrast, although at a lower level than that of SEQ ID NO:4 (FIGS. 2D and 2F). A systemic survey of animals injected with SEQ ID NO:25 revealed that all nerves were brightly labeled including cranial nerves (FIG. 2G-I). However, examination of nerves in the central nervous system (CNS) showed no evidence of labeling, perhaps due to lack of affinity of SEQ ID NO:4 for nerves in the CNS or the inability of the fluorescently labeled SEQ ID NO:4 to penetrate the blood brain barrier.

Peptide Binding Characteristics

Figure 3:
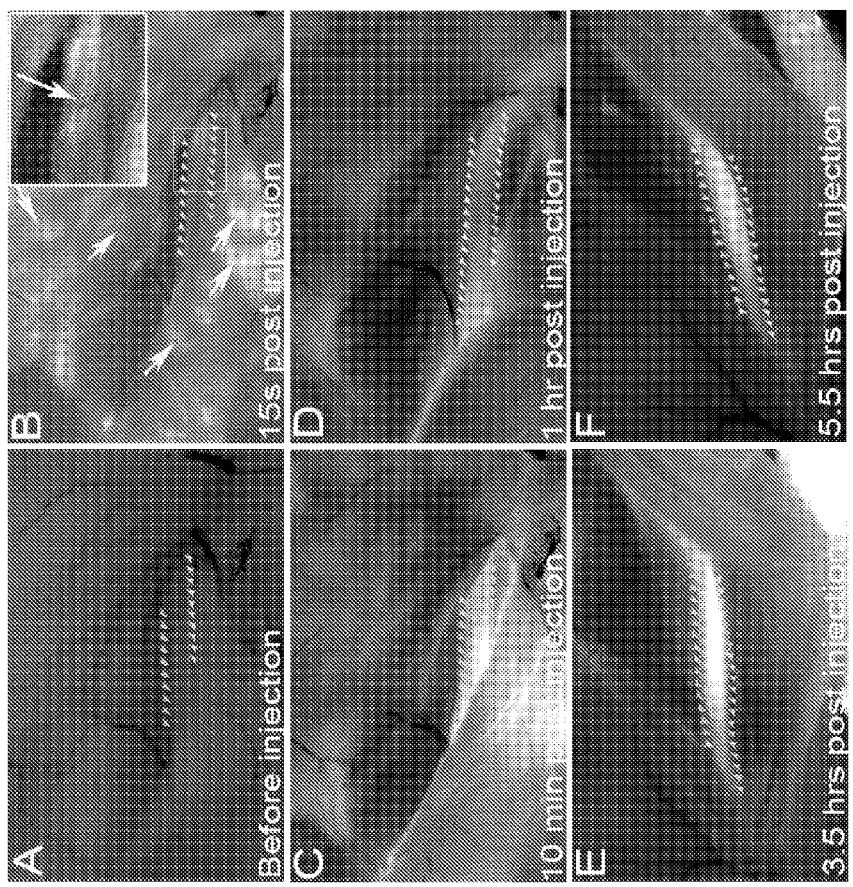
FIG. 3. Time course of SEQ ID NO:25 binding to nerve tissue. Fluorescence images of sciatic nerves and surrounding non-nerve tissue in living mice (A) prior to intravenous administration of SEQ ID NO:25; (B) 15 seconds post-injection; (C) 10 minutes post-injection; (D) 1 hr post-injection; (E) 3.5 hrs post-injection; and (F) 5.5 hrs post-injection.
Figure 4:
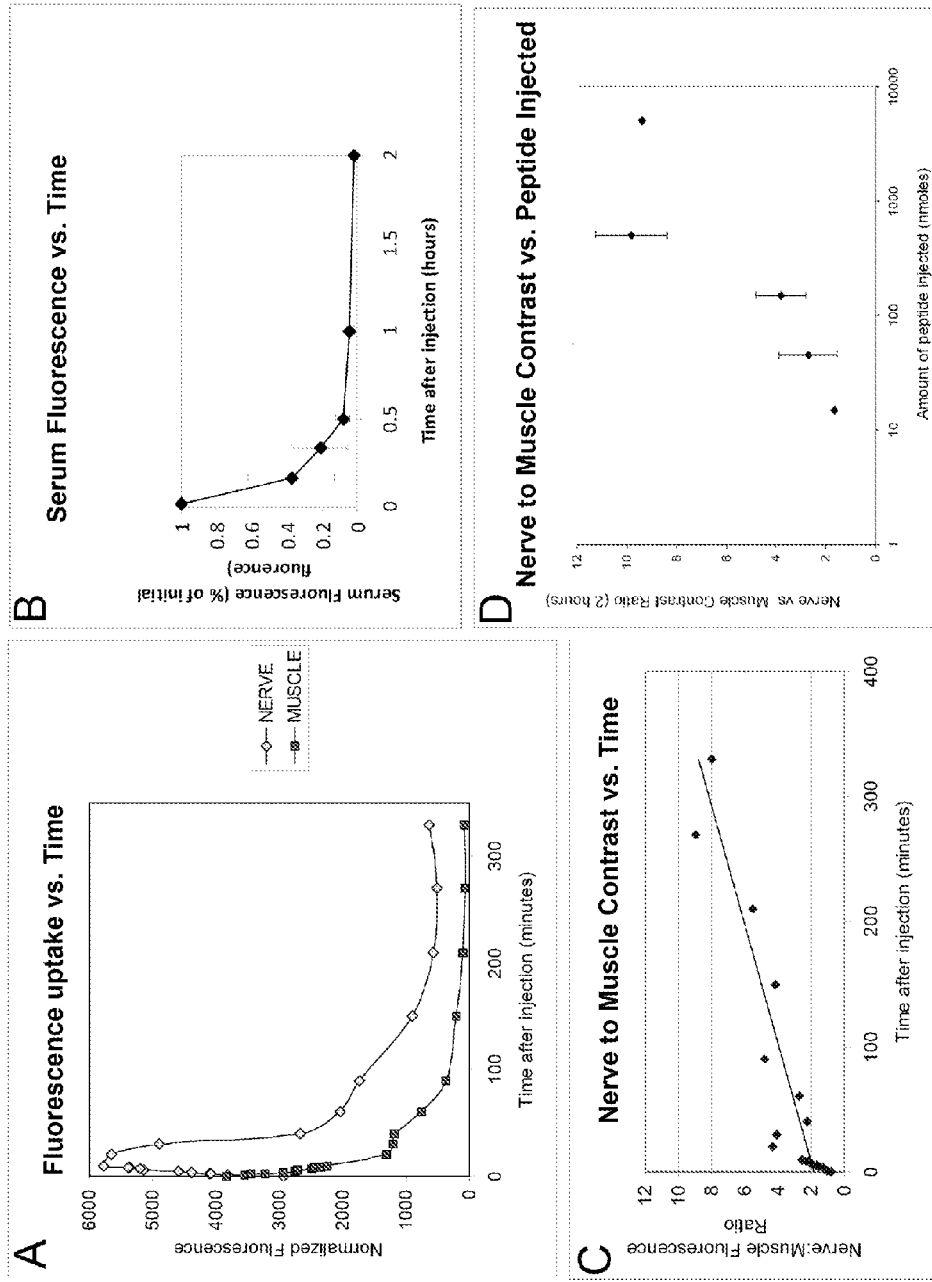
FIG. 4. Time course and dose response of SEQ ID NO:25 binding to nerve and non-nerve tissue. A. Amount of fluorescence uptake in nerve and non-nerve tissue in living mice was determined from the time of intravenous injection of SEQ ID NO:25 to 300 minutes post-injection. The half-life of nerve fluorescence was approximately 50 minutes, while the half-life of muscle fluorescence was approximately 20 minutes. B. Serum fluorescence was quantified from the time of intravenous injection to 2 hrs post-injection, measured as percentage of initial fluorescence. The half-life of serum fluorescence was approximately 10 minutes. C. Ratio of nerve fluorescence to muscle fluorescence was calculated from the time of intravenous injection to about 300 minutes post-injection. D. The dose response of peptide binding to nerve and muscle was determined by administering SEQ ID NO:25 at an amount ranging from 15 to 5,000 mmoles per mouse (average weight of mouse=25 g) and measuring ratio of nerve fluorescence to muscle fluorescence after 2 hrs.

To evaluate the time course of peptide binding to nerve tissue, sciatic nerves and surrounding non-nerve tissue in living mice were imaged before and after intravenous administration of SEQ ID NO:25, Prior to administration of SEQ ID NO: 25 (FIG. 3A), there was little contrast of the nerve (arrowheads) in relation to surrounding non-nerve tissue. Within seconds following intravenous administration of SEQ ID NO:25 (FIG. 3B), the fluorescent injectate could be seen leaking from capillaries (arrows), including capillaries associated with the sciatic nerves (insert). Nerve fluorescence peaked at around 10 minutes post-administration (FIG. 3C), and exhibited a steep decline thereafter (FIG. 4A; half life~50 minutes). Useful contrast between nerve and surrounding muscle begins to develop by 2-3 hours after intravenous injection (FIG. 3E) and lasts several hours (FIG. 3F). In contrast, muscle fluorescence was highest immediately following intravenous administration of the peptide, with a half life of ~20 minutes (FIG. 4A). Serum half-life was calculated at ~10 minutes. Nerve to muscle contrast ratio appeared to increase with time, with a contrast of 8-10 fold by 4-5 hours (FIG. 4C. By 24 his post-injection, all visible contrast between nerve and muscle had disappeared.

To determine the dose response of peptide binding, the nerve to muscle contrast ratio was measured as a function of the amount of peptide administered (FIG. 4D). It was found that nerve to muscle contrast ratio correlates to the amount of peptide administered in a sigmoidal fashion over the range of 15 to 5,000 nmoles injected per mouse (average weight 25 g).

Toxicity and Motor Function

To evaluate generalized toxicity following peptide administration, the generalized activity, behavior and weight gain of mice after a single intravenous injection of 15-5,000 nmoles of SEQ ID NO:25 was studied. It was find that the mice did not have any apparent changes in behavior, generalized activity or weight gain following injection with FAM-NP41 at any of doses given, as compared to uninjected mice, for up to 8 weeks of monitoring (n=2 at 15 nmoles; n=2 at 45 nmoles; n=60 at 150 motes; n=2 at 450 nmoles; and n=2 at 5.000 mmoles).

Figure 8:
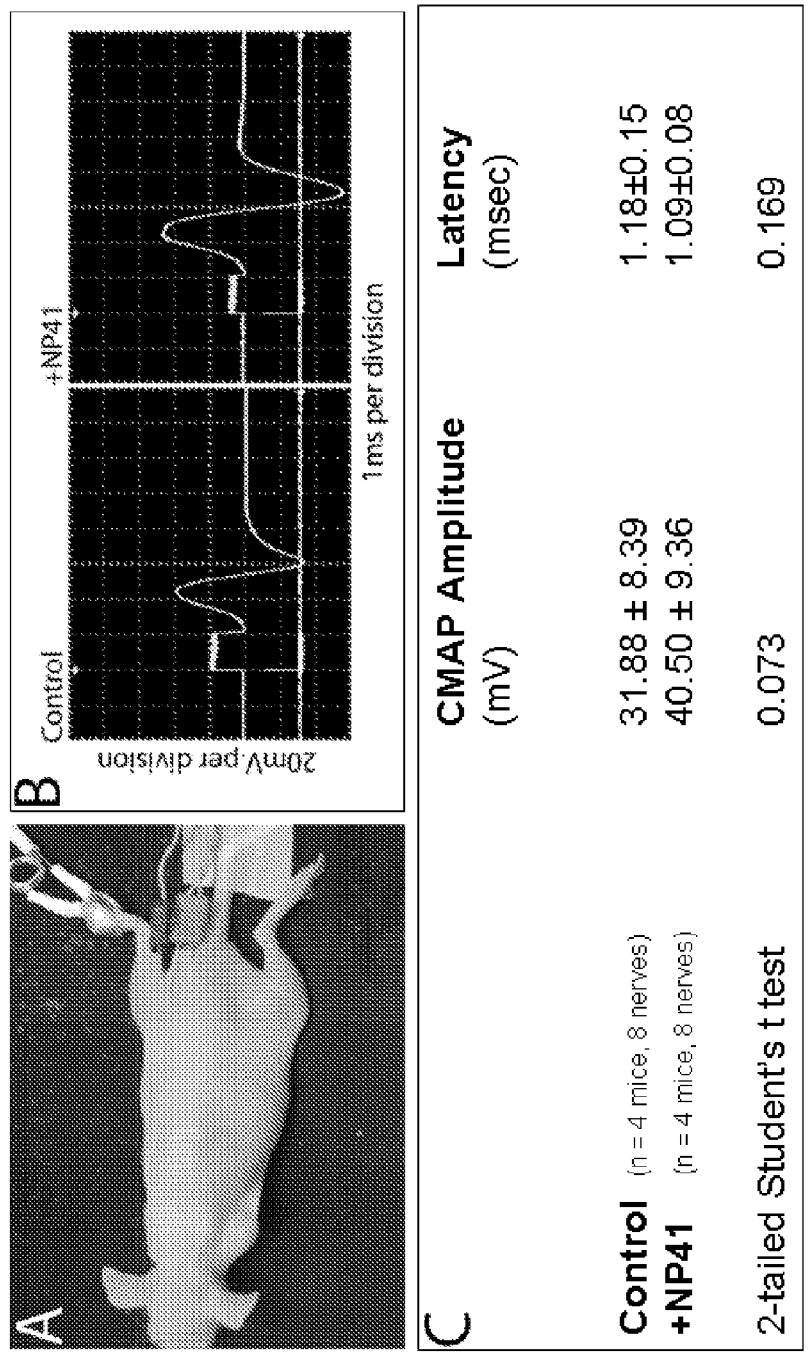
FIG. 8 Nerve conduction studies. A. Compound muscle action potentials (CMAP) were evoked with stimulating electrodes (orange) placed 2 mm lateral to the midline. The recording electrode was an ear-clip electrode placed on the digits of the hind foot and the reference electrode (purple) was placed on the heel of the foot. B. Representative CMAP tracing for control (left panel) and SEQ ID NO:25-treated (right panel) animals. C. 2-tailed Student's t test results showing that there is no significant difference between the CMAP amplitude and latency between control and SEQ ID NO: 4-treated nerves.
Figure 9:
FIG. 9. Illustrates the chemical structure of one isomer of SEQ ID NO:89.

To evaluate nerve function after the administration of SEQ ID NO:4, we performed nerve conduction studies to evaluate maximal compound muscle action potential (CMAP) amplitude and latency (FIG. 8A). We found that the shape of the CMAP curve is similar between control and SEQ ID NO:4-treated animals (FIG. 8B). CMAP amplitude and latency were also similar between control and SEQ ID NO:4-treated animals (FIG. 8C).

Peptide Metabolism

To evaluate the biodistribution of the peptide following systemic administration, organs were harvested from mice treated with SEQ ID NO:4 and fluorescence uptake was evaluated. The majority of the peptide accumulated in the kidney and was excreted into the urine. To evaluate the metabolism of the peptide as it passed through the renal system, liquid chromatography-mass spectrometry (LC-MS, Agilent) tracing was used to compare urine obtained from mice injected with SEQ ID NO:25 or SEQ ID NO:31 intravenously versus urine from normal mice spiked with the native SEQ ID NO:25 or SEQ ID NO:31. It was found that SEQ ID NO:25 and SEQ ID NO:31 were modified as they passed through the renal system, as none of the native SEQ ID NO:25 or SEQ ID NO:31, was detectable in urine from mice injected intravenously with SEQ ID NO:25 or SEQ ID NO:31. Next, matrix-assisted. laser desorption/ionization (MALDI) was used to evaluate the nature of the modification to the peptide as it was metabolized. The only fluorescently labeled entity identified was the lysine-FAM or cysteine-Cy5, suggesting either that the entire peptide had been degraded or that there was cleavage precisely between the terminal glycine amino acid and the lysine-FAM or cysteine-Cy5.

Effect of Nerve Injury on Labeling

The ability of peptides to label peripheral nerves following nerve crush injury was evaluated in mice using SEQ ID NO:25. We found that nerve labeling was intact compared to the contralateral control nerve 1 day after crush injury, decreased by 40% 3 days after injury, and returned to control levels 7 days after injury (FIG. 6A-F,I). We plan to perform systemic evaluation of proteins that are downregulated following crush injury with a similar time course to obtain insight into the binding target. for SEQ ID NO:4. (Occasionally, nerve labeling immediately at the site of injury was slightly diminished compared to nerve labeling several centimeters away from the site of injury (FIG. 6D), but this observation was highly variable (FIGS. 6B,F) and not statistically significant (FIG. 6I)). Nerve fluorescence was highly diminished compared to the contralateral control side immediately following nerve devascularization (by intentional injury to the feeding vessels, FIG. 6G-H), presumably due to the lack of peptide access to the nerve from the devascularization procedure.

Histology

Figure 5:
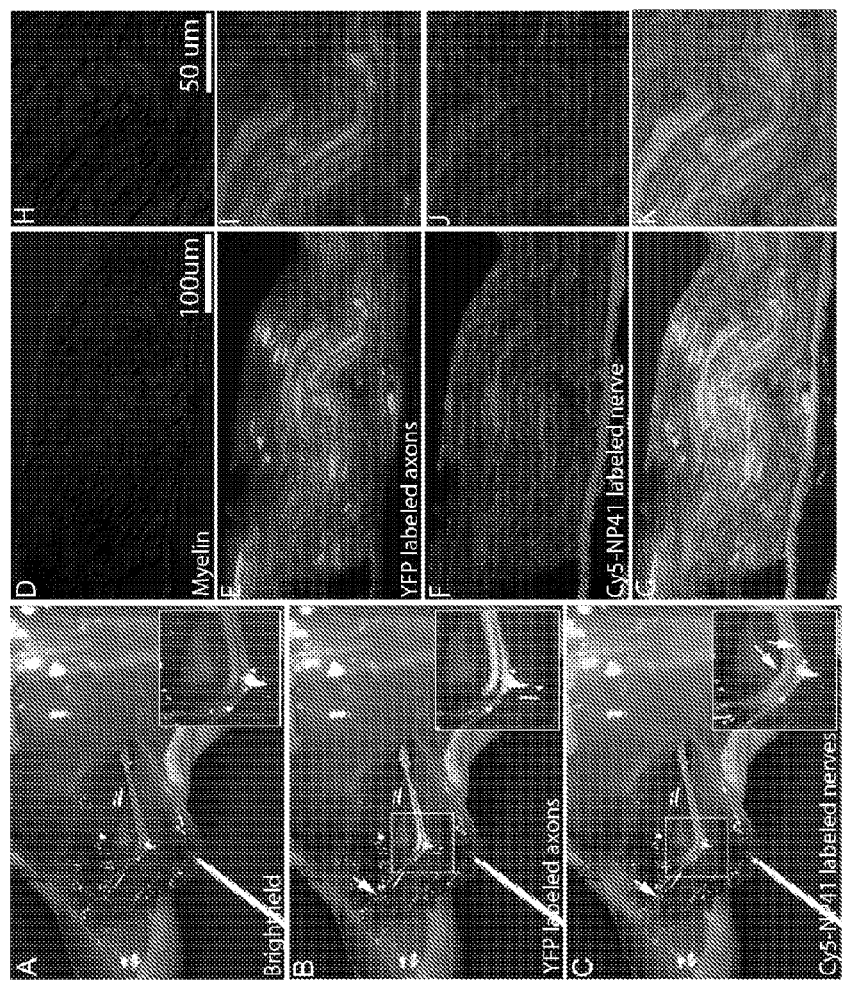
FIG. 5. SEQ ID NO:31-(ACETYL-SHSNTQTLAKAPE-HTG-(L-cys)-(Cy5)-amide) labeling of sciatic nerve in thy1-YFP transgenic mice, A. Low power brightfield view of left exposed sciatic nerve. B. Same nerve as in A viewed with YFP fluorescence superimposed on the brightfield image showing the transgene expression of YFP in axons. C. Same nerve as in A and B viewed with Cy5 fluorescence superimposed on the brightfield image showing nerve labeling with SEQ ID NO:31. D. Low magnification photomicrograph showing myelin within the sciatic nerve using Nomarski optics. E. Same nerve as in E showing YFP-labeled axons. F. Same nerve as in D and E, showing SEQ ID NO:31 labeling of epineurium, perineurium and endoneurium. G. Composite image of E, D and F showing that SEQ ID NO: 4 labeling does not colocalize with either myelin or axons. H-K, Higher magnification of panels E-G.
Figure 6:
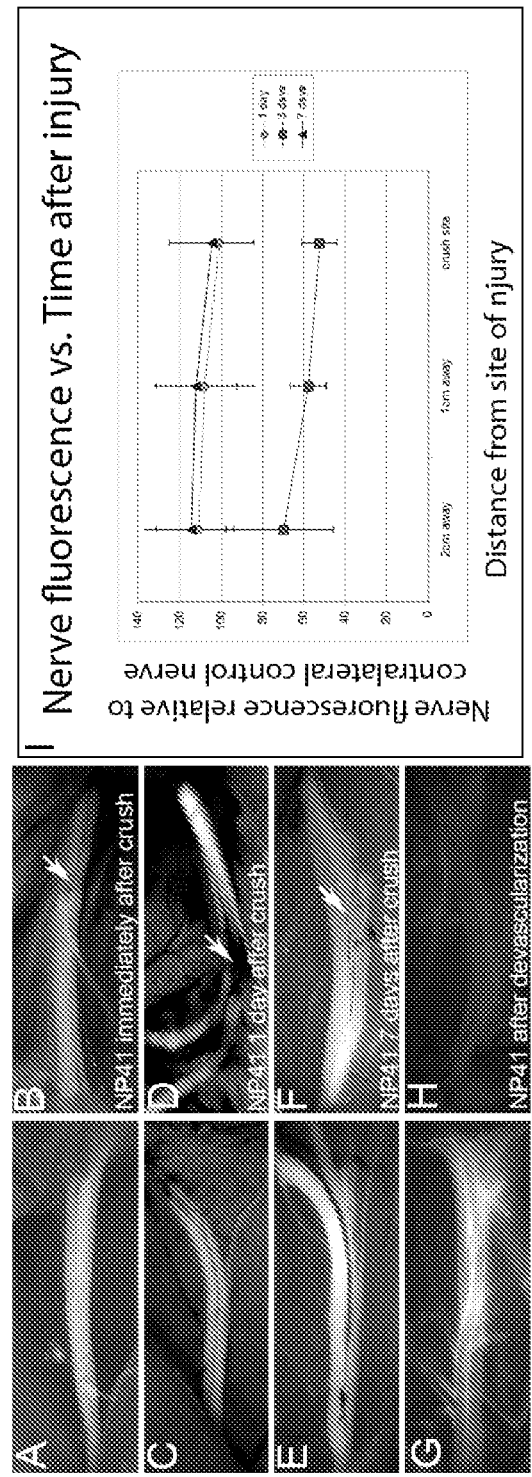
FIG. 6. Nerve labeling with SEQ ID NO:4 following injury. Nerve labeling with SEQ ID NO:4 is diminished at 3 days following injury but recovers by 7 days after injury. A-F, SEQ ID NO:4 labeling of representative sciatic nerves in control nerves (A,C,E,G) and immediately after crushing (B), 1 day after crushing (D), 7 days after crushing (F) and after devascularization (H). I. Graph showing that a) nerve fluorescence does not significantly diminish as a function of distance from crush site and b) nerve fluorescence is significantly diminished by day 3 after crush but then recovers to that equal to contralateral control nerve by day 7 after crush.

To evaluate the localization of SEQ ID NO:4 binding in nerves, we treated thy1-YFP transgenic mice whose axons are genetically encoded with YFP under a neuron specific promoter (Feng et al, Imaging neuronal subsets in transgenic mice expressing multiple spectral variants of GFP. Neuron, 2000) with SEQ ID NO:31. We found that SEQ ID NO:31 (FIG. 5C) precisely labels nerves that are genetically encoded with YFP (FIG. 5B) and as seen with brightfield imaging (FIG. 5A). In addition, because SEQ ID NO:31 has deeper tissue penetration compared to imaging in the visible range (brightfield or YFP), we were able to observe nerves that were branching deep into the muscle, away from the field of view in the SEQ ID NO:31 animals (FIG. 5C, insert arrows). These deeper nerve structures were not easily seen either with brightfield (FIG. 5A, insert) or YFP (FIG. 5B, insert) imaging. To evaluate the localization of SEQ ID NO:4 binding on a cellular level, we imaged cryosections (3-5 μm) of nerves and attached muscles from thy1-YFP animals treated with SEQ ID NO:31. We found that SEQ ID NO:31 appears to be most localized to the epineurium of the nerves with some labeling of the perineurium and endoneurium (FIG. 5F,J). We also found that SEQ ID NO:4 labeling (FIG. 5F,J) does not appear to colocalize with either myelin (FIG. 5D, H) or axons (FIG. 5 E,I). We plan to perform a systemic evaluation of proteins that exhibit a similar pattern of localization to obtain insight into the binding target for SEQ ID NO:4.

Human Nerve Labeling

Figure 7:
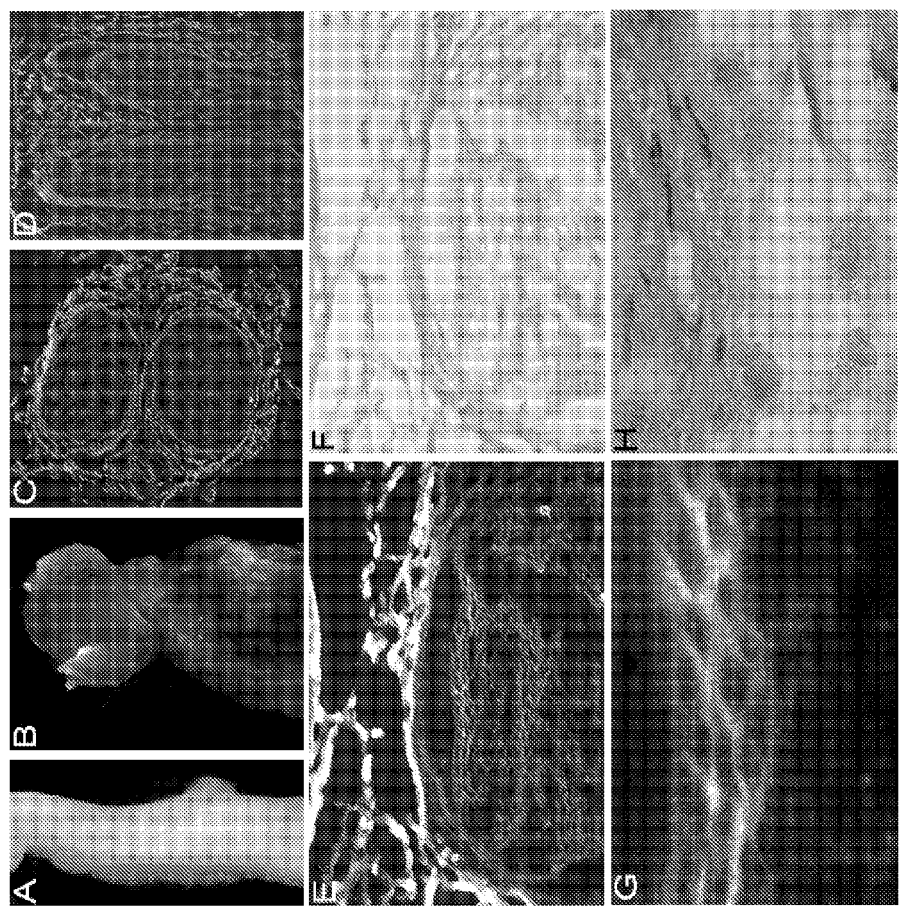
FIG. 7. Human nerve labeling with SEQ ID NO:4. (A) Fluorescence images of human recurrent laryngeal nerve and (B) human muscle freshly resected from patient undergoing total laryngectomy incubated with SEQ ID NO: 25. Fluorescent photomicrograph of human nerve in cross-section (C) and longitudinal section (D). High-power fluorescent photomicrograph of human nerve (E,G). Hematoxylin/eosin stain of same sections (F,H).

To evaluate whether or not SEQ ID NO:25 could selectively bind human nerves as compared to non-nerve tissue, freshly resected recurrent laryngeal nerves and adjacent muscle obtained from patients undergoing total laryngectomy for laryngeal cancer were incubated with SEQ ID NO:25. Selective binding of SEQ ID NO:25 to nerves as compared to adjacent muscle was observed (FIG. 7A-B). Histological examination of tissue sections showed that the pattern of nerve binding in human tissue appeared to be to the connective tissue surrounding the nerve, i.e. epineurium, perineurium, and endoneurium (FIG. 7C-H). This binding pattern is similar to the binding pattern observed in mice.

Example 2

Materials and Methods

Peptide Selection with Phage Display

Phage display screens were used for in vitro selection of peptides binding to excised murine peripheral nerves or purified myelin basic protein (MBP) and for an in vivo selection screen in which the phage library was injected in the tail vein of mice followed by dissection of nerve tissue and isolation of phage.

For the in vitro selection, m13 phage libraries expressing random 12 amino acid sequences on the N-terminus of gIII (New England Biolabs) were processed through two parallel selections for binding to either purified MBP or to excised murine peripheral nerves. In the selection against MBP, phage expressing a library of peptide were selected through multiple cycles for binding to biotinylated MBP using avidin agarose to isolate selected phage. Specifically, phage library was mixed with biotinylated MBP and allowed to bind for 1 hour. Avidin agarose was added and incubated for an additional hour. Non-binding phage were removed by washing agarose 3 times with phosphate buffered saline solution (PBS), and the supernatant was plated for titer and amplification for subsequent cycles. This process was repeated 5 times; once repeat sequences appeared, these were synthesized for affinity testing.

In the selection against excised murine peripheral nerves, phage from the same library as the selection against MBP were isolated based on differential binding to excised murine peripheral nerves and not to adjacent muscles and fat tissue. Phage were processed through multiple cycles of selection, with representative phage being isolated and sequenced after each cycle. Specifically, for positive selection using nerve tissue, neural tissue was dissected/washed and mixed with phage library. Following incubation, the mixture (containing mostly intact nerves with phage particles that had variable affinity for nerves) was centrifuged and the pellet washed with PBS. The pellet was homogenized and plated for titering and re-amplification. For negative selection using non-nerve tissues (e.g., muscle and fat), non-nerve tissues were dissected from normal mice and incubated with the phage library obtained from the positive selection. Following the incubation period, the mixture was centrifuged and the supernatant plated for titer and sequencing. Once individual sequences started to appear repetitively, these were re-synthesized for affinity testing.

For the in vivo selection, the same phage library as for the in vitro selections was injected in the tail vein of mice followed by dissection of nerve tissue and isolation of phage. In each case isolated phage were re-amplified and re-injected to iterate each selection step up to 8 times. Specifically, phages were injected into wild-type mice. Following a binding/washout period of 2-4 hours, the mice were sacrificed and nerve tissue (sciatic, brachial plexus, cranial nerves) were dissected, washed, and homogenized. Homogenates were plated for titering and re-amplified for subsequent injections. Sample phage were sequenced after each round of selection. Once repeat sequences appeared, they were synthesized for affinity testing.

Amino acid sequences derived from sequences of selected phage were chemically synthesized as peptides by solid-phase synthesis and labeled with fluorescein or Cy5 for in vitro testing and in vivo labeling of nerves. Selected peptides were additionally attached to other fluorescent dyes and in some case conjugated to a large molecular weight carrier such as (dextran) to increase the multivalency and avidity of the peptide. Derivatives of SEQ ID NO:4 peptides that were made and tested are listed in Table 2, ID NO:25 via, tail vein injection. Sequential fluorescence imaging was then performed as described above: excitation 470/40 nm, emission 525/50 nm, exposure 15 milliseconds-5 seconds. Nerves and adjacent non-nerve tissue were delineated with Image J and relative fluorescence was measured.

TABLE 2

Nerve contrast with derivatives of peptide SEQ ID NO: 4

| Peptide | Nerve contrast |
| --- | --- |
| acetyl- SHSNTQTLAKAPEHTGK (5,6FAM)-amide (SEQ ID NO: 25) | High |
| acetyl- SHSNTQTLA-(acetyl-lysine)-APEHTGK (5,6FAM)-amide (SEQ ID NO: 45) | Medium/High |
| All D-amino acid acetyl- SHSNTQTLAKAPEHT-GK-(5,6FAM)-amide | Medium |
| acetyl- SHSNTQTLAKAPEHTG(L-cys)(5,6FAM)-amide (SEQ ID NO: 46) | Medium/High |
| Free amine- SHSNTQTLAKAPEHTG-(L-cys)-(5,6FAM)-amide (SEQ ID NO: 47) | Medium/High |
| acetyl- SHSNTQTLAKAPEHTG-(D-cys)-(5,6FAM)-amide | Medium |
| acetyl- SHSNTQTLAKAPEHTG-(L-cys)-(cy5)-amide (SEQ ID NO: 31) | Medium/High |
| acetyl- SHSNTQTLAKAPEHTG-(D-cys)-(cy5)-amide | Medium |
| acetyl- SHSNTQTLAKAPEHTG-(L-cys)-(IR800CW) (SEQ ID NO: 48) | Low |
| acetyl- SHSNTQTLAKAPEHTG-(L-cys-)-(TAMRA)-amide (SEQ ID NO: 49) | Medium |
| acetyl- SHSNTQTLAKAPEHTG-(L-cys)-(Texas Red)-amide (SEQ ID NO: 50) | Medium |
| acetyl- SHSNTQTLAKAPEHTG-(L-cys)-(indocyanine green derivative) (SEQ ID NO: 51) | Low |
| acetyl- SHSNTQTLAKAPEHTG-(L-cys)-(heptamethinecyanine derivative) (SEQ ID NO: 52) | Low |

Testing of Nerve Binding with Fluorescently Labeled Peptides

Wild-type albino C57BL6 (Jackson Laboratory) or SKH1 (Charles River Laboratories) mice were treated intravenously with 150 nmoles of fluorescently labeled SEQ ID NO:4 via tail vein injection. Following a 2-3 hour wash-out period for SEQ ID NO:25 or 5-6 hours for SEQ ID NO:31, mice were anesthetized with ketamine and midazolam (80 mg/kg intraperitoneally), a skin incision was made over the dorsal surface of the hind, legs and the sciatic nerves exposed bilaterally. Fluorescent images were acquired with a dissecting microscope (Lumar Zeiss) and a monochrome camera (Coolsnap), excitation 470/40 nm, emission 525/50 nm for SEQ ID NO:25 and excitation 620/60, emission 700/75 for SEQ ID NO:31, 5-10 second exposure. Nerves and adjacent non-nerve tissue was delineated with Image J and relative fluorescence was measured. Following background subtraction using dark current measurements and measurements of a standard, the ratios of peptide binding to nerve versus adjacent non-nerve tissue were calculated.

Time Course of Nerve Binding

Female 8 week-old SKH1 mice were anesthetized with ketamine and midazolam and a skin incision was made over the dorsal surface of the hind legs and the sciatic nerves exposed. A preinjection image was taken a dissecting microscope (Lumar Zeiss) and a monochrome camera (Coolsnap). The mice were treated intravenously with 150 moles of SEQ ID NO:25 via, tail vein injection. Sequential fluorescence imaging was then performed as described above: excitation 470/40 nm, emission 525/50 nm, exposure 15 milliseconds-5 seconds. Nerves and adjacent non-nerve tissue were delineated with Image J and relative fluorescence was measured. Quantification of fluorescence was then performed following subtraction of dark current and normalizing to a standard.

Dose Response of Peptide Binding

Female 8 week-old SKH1 mice (average weight 25 g) were treated with varying amounts of SEQ ID NO:25 ranging from 15-5.000 mmoles. After a 2 hour washout period, mice were sacrificed and sciatic nerves exposed. Nerves and adjacent non-nerve tissue were delineated with Image 3 and relative fluorescence was measured. Quantification of fluorescence was then performed following subtraction of dark current and normalizing to a standard. For the mice injected with 5,000 nmoles of SEQ ID NO:4, it was noted that background fluorescence was still very high at 2 hours, making the contrast ratio low even though the absolute nerve fluorescence was high. For these mice, the skin incisions were repaired and the mice were allowed to awaken from anesthesia, then at 6 hours following initial SEQ ID NO:4 administration, the mice were sacrificed and the sciatic nerves exposed and analyzed as above.

Toxicity and Motor Function

Female 8 week-old SKH1 mice (average weight 25 g) were treated with varying amounts of SEQ ID NO:25 ranging from 15-5,000 nmoles. Generalized activity, behavior and weight gain were evaluated following single intravenous injection of 15-5,000 nmoles of SEQ ID NO:4 on a daily basis for 3 clays following injection. Thereafter, the mice were monitored three times per week for 8 weeks. We found that generalized activity, behavior and weight gain were similar between SEQ ID NO: 4-treated and control mice.

Nerve Conduction Studies

Maximal compound muscle action potential amplitude (CMAP) and nerve conduction latency were measured as described in Osuchowski et al, Noninvasive model of sciatic nerve conduction in healthy and septic mice: reliability and normative data, *Muscle Nerve,* 2009), Briefly, control female 8 week-old SKH1 mice and mice treated with SEQ ID NO:25 were anesthetized with ketamine-midazolam and placed in a prone position. CMAP potentials were evoked (Grass stimulator) with stimulating electrode (Medtronics) placed 2 mm lateral to the midline. The recording electrode was an ear-clip electrode (Life-tech.com) placed on the digits of the hind foot and the reference electrode was placed on the heel of the foot. Maximal CMAPs were generated by gradually increasing the stimulation (5-10V, 1 pulse per second, paired, 0.5-2 sec duration) until a maximal, artifact free tracing was obtained. The CMAP traces were captured on a digital oscilloscope (Tektronic). Nerve conduction latency was measured from the beginning of the stimulation to the start of the upslope. CMAP amplitude was measured from the start of the upslope to the peak.

Peptide Metabolism

To evaluate the biodistribution of the peptide following systemic administration, organs were harvested from mice treated with SEQ ID NO:4 and fluorescence uptake was evaluated. The majority of the peptide accumulated in the kidney and was excreted into the urine. To evaluate the metabolism of the peptide as it passed through the renal system, liquid chromatography-mass spectrometry (LC-MS, Agilent) tracing was used to compare urine obtained from mice injected with SEQ ID NO:25 and SEQ ID NO:3 intravenously versus urine from normal mice spiked with the native SEQ ID NO:25. It was found that SEQ ID NO:25 and SEQ ID NO:31 were modified as they passed through the renal system, as none of the native SEQ ID NO:25 or SEQ ID NO:31 was detectable in urine from mice injected intravenously with SEQ ID NO:25 or SEQ ID NO:31. Next, matrix-assisted laser desorption/ionization (MALDI) was used to evaluate the nature of the modification to the peptide as it was metabolized. The only fluorescently labeled entity identified was the lysine-FAM or cysteine-Cy5 respectively, suggesting either that the entire peptide had been degraded or that there was cleavage precisely between the terminal glycine amino acid and the lysine-FAM or cysteine-Cy5.

Effect of Nerve Injury on Labeling

Wild type mice were anesthetized and the left sciatic nerve exposed and crushed with microforceps for 3-5 seconds. Muscular contractions during the crush after immediately afterwards were monitored to ensure uniformity of the injury. The skin incision was then closed and mice returned to their cages to recover. At varying times after crush injury, intravenous SEQ ID NO:25 (150 nmoles) was administered. Two to three hours after intravenous SEQ ID NO:25 treatment, the mice were anesthetized, bilateral sciatic nerves exposed and quantitative fluorescence microscopy was used to measure nerve fluorescence. Nerve and adjacent muscle fluorescence were measured using Image J software by measuring standardized boxed regions. Crushed and contralateral control nerve fluorescence were compared for each animal.

Human Nerve Labeling

To evaluate whether or not SEQ ID NO:25 could selectively bind human nerves as compared to non-nerve tissue, freshly resected recurrent laryngeal nerves and adjacent muscle obtained from patients undergoing total laryngectomy for laryngeal cancer were incubated with SEQ ID NO:25 at 50 µm for 15 minutes and washed in saline for 15 minutes each. The nerve and muscle segments were then placed on a black non-fluorescent plate and imaged (Maestro, CRI). The nerve segments were then embedded in Tissue-Tek®, frozen and cryosectioned. 7-10 µm cryosections were then. imaged with standard fluorescence microscopy. Adjacent sections were stained with hematoxylin and eosin (H&E) and imaged.

Example 3

Selection of Aptamers for Nerve Labeling

For the in vivo and in vitro selection, three aptamer libraries were processed through two parallel selections for binding to either excised murine nerves or in-vivo uptake into nerves after IV injection.

```
                                              (SEQ ID NO: 53)
a. Library 1: (N60) EcoR1-N60-EcoR1
GGACGCGGAATTCCGACTCGNNNNNNNNNNNNNNNNNNNNNNNNNNNNNN

NNNNNNNNNNNNNNNNNNNNNNNNNNNNNNNNCTCATCGGAATTCCGC

GTCC
                                              (SEQ ID NO: 54)
b. Library 2 (N50)- EcoR1-N50-EcoR1
GGACGCGGAATTCCGATTACNNNNNNNNNNNNNNNNNNNNNNNNNNNNN NNNNNNNNNNNNNNNNNNNNNNNCAGACCGGAATTCCGCTCC
                                              (SEQ ID NO: 55)
c. Library 3 (3N20) EcoR1-N20-Xba-N20-Xba-N20EcoR1
GGACGCGGAATTCCGCCGTCNNNNNNNNNNNNNNNNNNNNNGCTCTAGA

GCNNNNNNNNNNNNNNNNNNNNGCTCTAGAGCNNNNNNNNNNNNNNNN

NNNNGATACCGGAATTCCGCGTCC
```

For in vitro selection of nerve binding aptamers, aptamer were selected for binding to excised nerves over multiple rounds of iterative selection. Specifically, excised nerves (both cranial and peripheral) were mixed separately with each of the 3 aptamer libraries and allowed to bind to nerve under fixed condition followed by washing and re-amplification. For rounds 1-3 nerves and aptamers were incubated at 4° C. for 18 hours followed by three wash cycles in PBS at 4° C. For rounds 4-6 nerves and aptamers were incubated a 21° C. for 2 hours followed by 5 washes with PBS at 21° C. In each case aptamers were eluted from nerve by heating for 10 min to 95° C. in PBS with Chelex, an ion exchange resin which removes polyvalent metal ions. After selection and elution, aptamers were reamplified prior to the next round of selection. Post PCR aptamers were boiled and rapidly cooled prior to re-injection. After 5 rounds of binding and re-amplification single representative were sequenced. A partial list is listed below. Sequences of aptamers recovered from the EcoR1-N50-EcoR1 aptamer library (i.e.

```
                                              (SEQ ID NO: 54)
GGACGCGGAATTCCGATTACNNNNNNNNNNNNNNNNNNNNNNNNNNNNN

NNNNNNNNNNNNNNNNNNNNNNNCAGACCGGAATTCCGCTCC) selection
were:

a. MC-m2-a
1. GAATTC CGGTCTG GAGGACCGGATGGCAAAAATATCTAAAAAA

CACAGAATAA AACGTTATTG (SEQ ID NO: 56)

2. GTAATCGGAATTC (SEQ ID NO: 57)

b. MC-m2-b
```

-continued

```
                                       (SEQ ID NO: 58)
1. GAATTC CGATTAC CACAAATTCGTTACATGCTC CTCTATCGCG

2. CCTTCCTTCC GTCCGC (SEQ ID NO: 59)

3. CAGACCGGAATTC (SEQ ID NO: 60)

c. MC-m2-c
1. GAATTCCGGTCTG (SEQ ID NO: 61)

2. GGAACAGACC GGCCTCTTAT TGTGGTTTCG GCTTGGTTAG

CGGGTG (SEQ ID NO: 62)

3. GTAATCGGAATTC (SEQ ID NO: 63)

d. MC-m2-d
1. GGAATTCCGATTAC (SEQ ID NO: 64)

2. CGACGTGTCTACCTTCATTTACTGTCCCCATCGTCCCCCGGGTTGG

TCCCAGACCGGAATTC (SEQ ID NO: 65)

e. MC-m2-e
1. GAATTCCGATTAC (SEQ ID NO: 66)

2. CATAGTTATGTCGTGTCTCTAGGTCATCCTTCCTCGTCATTCCCGG

TCCCA (SEQ ID NO: 67)

3. GACCGGAATTC (SEQ ID NO: 68)
```

Sequences of aptamers (variable library region in non-bold) recovered from the EcoR1-N20-Xba-N20-Xba-N20-EcoR1 aptamer library (i.e.

```
                                              (SEQ ID NO: 55)
GGACGCGGAATTCCGCCGTCNNNNNNNNNNNNNNNNNNNNGCTCTAGAG

CNNNNNNNNNNNNNNNNNNNNGCTCTAGAGCNNNNNNNNNNNNNNNNNNNN

NNGATACCGGAATTCCGCGTCC) selections were:

a. MC-m3-a
1. GAATTCCGCCGTC (SEQ ID NO: 69)

2. GGCGGGACCTGGGCTATGTT (SEQ ID NO: 70)

3. GCTTTAGAG (SEQ ID NO: 71)

4. CCCGGAAGGCAGGGGTAATA (SEQ ID NO: 72)

5. GCTCTAGAG (SEQ ID NO: 73)

6. CCAGGAGAGGTGTGGGGGTG (SEQ ID NO: 74)

7. GATACCGGAATTC (SEQ ID NO: 75)

b. MC-m3-b
1. GAATTCCGCCGTC (SEQ ID NO: 76)

2. GGCGGACGACCCTCAGTTCG (SEQ ID NO: 77)

3. GCTCTAGGAG (SEQ ID NO: 78)

4. CAATATTAATCCTCATGGGCC (SEQ ID NO: 79)

5. GCTCTAGAG (SEQ ID NO: 80)

6. CTCGCACTTTTTTGTAATGTT (SEQ ID NO: 81)

7. GATACCGGAATTCC (SEQ ID NO: 82)
```

Sequences of aptamers (variable library region in non-bold) recovered from the EcoR1-N60-EcoR1 aptamer library (i.e.

```
GGACGCGGAATTCCGACTCGNNNNNNNNNNNNNNNNNNNNNNNNNNNNNN

NNNNNNNNNNNNNNNNNNNNNNNNNNNNNNNNCTCATCGGAATTCCGCGT

CC) (SEQ ID NO: 53) selection were:

a. m1a
1. GAATTCCGATGAG (SEQ ID NO: 83)

2. CACAATCTCAACCACGTCCCCAAGCAATGTAGCTTCCACGATTTAT

GGCCCGACTCGTCC (SEQ ID NO: 84)

3. CGAGTCGGAATTCC (SEQ ID NO: 85)

b. m1b
1. GAATTCCGATGAG (SEQ ID NO: 86)

2. CACAATCTCAACCACGTCCCCAAGCAATGTAGCTTCCACGATTTAT

GGCCCGACTCGTCC (SEQ ID NO: 87)

3. CGAGTCGGAATTCC (SEQ ID NO: 88)
```

Aptamers (as either pool or single sequences) were labeled with fluorescein using fluorescently labeled PCR primers and tested for binding to dissected nerve versus muscle tissue.

In vivo selection for aptamer binding to nerves: For the in vivo selection the N60 aptamer library was injected in the tail vein of mice followed by dissection of nerve tissue.

Dissected tissues were washed mixed with chelex, boiled and used for PCR reamplification. After selection and elution, aptamers were reamplified prior to the next round of selection.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

---

SEQUENCE LISTING

<160> NUMBER OF SEQ ID NOS: 89

<210> SEQ ID NO 1
<211> LENGTH: 12
<212> TYPE: PRT
<213> ORGANISM: Artificial Sequence
<220> FEATURE:
<223> OTHER INFORMATION: peptide that specifically binds to a neuron,
      nerve, or component of either

```
<400> SEQUENCE: 1

Ala His His Asn Ser Trp Lys Ala Lys His His Ser
1               5                   10

<210> SEQ ID NO 2
<211> LENGTH: 12
<212> TYPE: PRT
<213> ORGANISM: Artificial Sequence
<220> FEATURE:
<223> OTHER INFORMATION: peptide that specifically binds to a neuron,
      nerve, or component of either

<400> SEQUENCE: 2

Thr Tyr Thr Asp Trp Leu Asn Phe Trp Ala Trp Pro
1               5                   10

<210> SEQ ID NO 3
<211> LENGTH: 12
<212> TYPE: PRT
<213> ORGANISM: Artificial Sequence
<220> FEATURE:
<223> OTHER INFORMATION: peptide that specifically binds to a neuron,
      nerve, or component of either

<400> SEQUENCE: 3

Lys Ser Leu Ser Arg His Asp His Ile His His His
1               5                   10

<210> SEQ ID NO 4
<211> LENGTH: 12
<212> TYPE: PRT
<213> ORGANISM: Artificial Sequence
<220> FEATURE:
<223> OTHER INFORMATION: peptide that specifically binds to a neuron,
      nerve, or component of either

<400> SEQUENCE: 4

Asn Thr Gln Thr Leu Ala Lys Ala Pro Glu His Thr
1               5                   10

<210> SEQ ID NO 5
<211> LENGTH: 11
<212> TYPE: PRT
<213> ORGANISM: Artificial Sequence
<220> FEATURE:
<223> OTHER INFORMATION: peptide that specifically binds to a neuron,
      nerve, or component of either

<400> SEQUENCE: 5

Asp Phe Thr Lys Thr Ser Pro Leu Gly Ile His
1               5                   10

<210> SEQ ID NO 6
<211> LENGTH: 12
<212> TYPE: PRT
<213> ORGANISM: Artificial Sequence
<220> FEATURE:
<223> OTHER INFORMATION: peptide that specifically binds to a neuron,
      nerve, or component of either

<400> SEQUENCE: 6

Leu Thr Pro Ile Pro Leu Pro Thr Pro Lys Pro Pro
1               5                   10

<210> SEQ ID NO 7
<211> LENGTH: 12
<212> TYPE: PRT
```

```
<213> ORGANISM: Artificial Sequence
<220> FEATURE:
<223> OTHER INFORMATION: peptide that specifically binds to a neuron,
      nerve, or component of either

<400> SEQUENCE: 7

Val Ser Thr Met Pro Met Ser Asn Met Asn Gly Pro
1               5                   10

<210> SEQ ID NO 8
<211> LENGTH: 12
<212> TYPE: PRT
<213> ORGANISM: Artificial Sequence
<220> FEATURE:
<223> OTHER INFORMATION: peptide that specifically binds to a neuron,
      nerve, or component of either

<400> SEQUENCE: 8

Gly Ile Phe Glu Arg Asn Phe Gly Ala Met Leu His
1               5                   10

<210> SEQ ID NO 9
<211> LENGTH: 10
<212> TYPE: PRT
<213> ORGANISM: Artificial Sequence
<220> FEATURE:
<223> OTHER INFORMATION: peptide that specifically binds to a neuron,
      nerve, or component of either

<400> SEQUENCE: 9

Ala Cys Leu Arg Glu Tyr His Asn Trp Cys
1               5                   10

<210> SEQ ID NO 10
<211> LENGTH: 12
<212> TYPE: PRT
<213> ORGANISM: Artificial Sequence
<220> FEATURE:
<223> OTHER INFORMATION: peptide that specifically binds to a neuron,
      nerve, or component of either

<400> SEQUENCE: 10

Met His Arg Gln Pro Ile Ala Pro Val Ser Ser Leu
1               5                   10

<210> SEQ ID NO 11
<211> LENGTH: 12
<212> TYPE: PRT
<213> ORGANISM: Artificial Sequence
<220> FEATURE:
<223> OTHER INFORMATION: peptide that specifically binds to a neuron,
      nerve, or component of either

<400> SEQUENCE: 11

Ser Phe Ala Asp Pro Leu Leu Phe Leu Ala Pro Pro
1               5                   10

<210> SEQ ID NO 12
<211> LENGTH: 12
<212> TYPE: PRT
<213> ORGANISM: Artificial Sequence
<220> FEATURE:
<223> OTHER INFORMATION: peptide that specifically binds to a neuron,
      nerve, or component of either

<400> SEQUENCE: 12

Ala Ser Ala His His Met Phe Thr Pro Gly Phe Asp
1               5                   10
```

```
<210> SEQ ID NO 13
<211> LENGTH: 12
<212> TYPE: PRT
<213> ORGANISM: Artificial Sequence
<220> FEATURE:
<223> OTHER INFORMATION: peptide that specifically binds to a neuron,
      nerve, or component of either

<400> SEQUENCE: 13

Val Ala Pro Thr Lys Ala Pro Leu His Ser Pro Ser
1               5                   10

<210> SEQ ID NO 14
<211> LENGTH: 12
<212> TYPE: PRT
<213> ORGANISM: Artificial Sequence
<220> FEATURE:
<223> OTHER INFORMATION: peptide that specifically binds to a neuron,
      nerve, or component of either

<400> SEQUENCE: 14

Asn Asn Leu Lys Thr Gly Thr Ser Ala Pro Thr Gly
1               5                   10

<210> SEQ ID NO 15
<211> LENGTH: 12
<212> TYPE: PRT
<213> ORGANISM: Artificial Sequence
<220> FEATURE:
<223> OTHER INFORMATION: peptide that specifically binds to a neuron,
      nerve, or component of either

<400> SEQUENCE: 15

His Lys Thr Ala Gln Trp Pro Phe Ile Ala Phe Arg
1               5                   10

<210> SEQ ID NO 16
<211> LENGTH: 12
<212> TYPE: PRT
<213> ORGANISM: Artificial Sequence
<220> FEATURE:
<223> OTHER INFORMATION: peptide that specifically binds to a neuron,
      nerve, or component of either

<400> SEQUENCE: 16

Arg Leu Thr Asn Ala Pro Ala Tyr Gln Ala Pro Ala
1               5                   10

<210> SEQ ID NO 17
<211> LENGTH: 11
<212> TYPE: PRT
<213> ORGANISM: Artificial Sequence
<220> FEATURE:
<223> OTHER INFORMATION: peptide that specifically binds to a neuron,
      nerve, or component of either

<400> SEQUENCE: 17

Met Gln Asn Pro Leu Asn Gly Lys Pro Gly Arg
1               5                   10

<210> SEQ ID NO 18
<211> LENGTH: 12
<212> TYPE: PRT
<213> ORGANISM: Artificial Sequence
<220> FEATURE:
<223> OTHER INFORMATION: peptide that specifically binds to a neuron,
      nerve, or component of either

<400> SEQUENCE: 18
```

```
Thr His Tyr Ser Arg Ser Leu Thr Asp Gly Thr Arg
1               5                   10

<210> SEQ ID NO 19
<211> LENGTH: 12
<212> TYPE: PRT
<213> ORGANISM: Artificial Sequence
<220> FEATURE:
<223> OTHER INFORMATION: peptide that specifically binds to a neuron,
      nerve, or component of either

<400> SEQUENCE: 19

Phe Ser Thr Ser Asn Asn Gln Ser Ser Pro Ala Ile
1               5                   10

<210> SEQ ID NO 20
<211> LENGTH: 12
<212> TYPE: PRT
<213> ORGANISM: Artificial Sequence
<220> FEATURE:
<223> OTHER INFORMATION: peptide that specifically binds to a neuron,
      nerve, or component of either

<400> SEQUENCE: 20

Tyr Pro Ser Pro Asn Arg Pro Pro Asn Leu Thr Asn
1               5                   10

<210> SEQ ID NO 21
<211> LENGTH: 12
<212> TYPE: PRT
<213> ORGANISM: Artificial Sequence
<220> FEATURE:
<223> OTHER INFORMATION: peptide that specifically binds to a neuron,
      nerve, or component of either

<400> SEQUENCE: 21

Asp Ile Ala Asn Pro Pro Pro Pro Leu Tyr Val
1               5                   10

<210> SEQ ID NO 22
<211> LENGTH: 12
<212> TYPE: PRT
<213> ORGANISM: Artificial Sequence
<220> FEATURE:
<223> OTHER INFORMATION: peptide that specifically binds to a neuron,
      nerve, or component of either

<400> SEQUENCE: 22

Ala Leu Gln Thr Asp Gly Pro Phe Ala Glu Ser Ala
1               5                   10

<210> SEQ ID NO 23
<211> LENGTH: 12
<212> TYPE: PRT
<213> ORGANISM: Artificial Sequence
<220> FEATURE:
<223> OTHER INFORMATION: peptide that specifically binds to a neuron,
      nerve, or component of either

<400> SEQUENCE: 23

Asp Asn Ala Gln His Ser Glu Arg Phe Pro Val Pro
1               5                   10

<210> SEQ ID NO 24
<211> LENGTH: 13
<212> TYPE: PRT
<213> ORGANISM: Artificial Sequence
<220> FEATURE:
```

```
<223> OTHER INFORMATION: peptide that specifically binds to a neuron,
      nerve, or component of either

<400> SEQUENCE: 24

Ile Pro Pro Thr Phe Pro Asp Arg Ile Arg Ala Pro Gly
1               5                   10

<210> SEQ ID NO 25
<211> LENGTH: 17
<212> TYPE: PRT
<213> ORGANISM: Artificial Sequence
<220> FEATURE:
<223> OTHER INFORMATION: fluorescent-labeled peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (17)..(17)
<223> OTHER INFORMATION: residue at this location is derivatized to
      N(epsilon)-[fluorescein-5(6)-carbonyl]-lysinamide

<400> SEQUENCE: 25

Ser His Ser Asn Thr Gln Thr Leu Ala Lys Ala Pro Glu His Thr Gly
1               5                   10                  15

Lys

<210> SEQ ID NO 26
<211> LENGTH: 17
<212> TYPE: PRT
<213> ORGANISM: Artificial Sequence
<220> FEATURE:
<223> OTHER INFORMATION: fluorescent-labeled peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (17)..(17)
<223> OTHER INFORMATION: residue at this location is derivatized to
      N(epsilon)-[fluorescein-5(6)-carbonyl]-lysinamide

<400> SEQUENCE: 26

Ser His Ser Ser Thr Ala Arg Asp Leu Trp Pro His Gly Lys Glu Gly
1               5                   10                  15

Lys

<210> SEQ ID NO 27
<211> LENGTH: 17
<212> TYPE: PRT
<213> ORGANISM: Artificial Sequence
<220> FEATURE:
<223> OTHER INFORMATION: fluorescent-labeled peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (17)..(17)
<223> OTHER INFORMATION: residue at this location is derivatized to
      N(epsilon)-[fluorescein-5(6)-carbonyl]-lysinamide

<400> SEQUENCE: 27

Ser His Ser Ala His His Asn Ser Trp Lys Ala Lys His His Ser Gly
1               5                   10                  15

Lys
```

```
<210> SEQ ID NO 28
<211> LENGTH: 17
<212> TYPE: PRT
<213> ORGANISM: Artificial Sequence
<220> FEATURE:
<223> OTHER INFORMATION: fluorescent-labeled peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (17)..(17)
<223> OTHER INFORMATION: residue at this location is derivatized to
      N(epsilon)-[fluorescein-5(6)-carbonyl]-lysinamide

<400> SEQUENCE: 28

Ser His Ser Thr Tyr Thr Asp Trp Leu Asn Phe Trp Ala Trp Pro Gly
1               5                   10                  15

Lys

<210> SEQ ID NO 29
<211> LENGTH: 17
<212> TYPE: PRT
<213> ORGANISM: Artificial Sequence
<220> FEATURE:
<223> OTHER INFORMATION: fluorescent-labeled peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (17)..(17)
<223> OTHER INFORMATION: residue at this location is derivatized to
      N(epsilon)-[fluorescein-5(6)-carbonyl]-lysinamide

<400> SEQUENCE: 29

Ser His Ser Lys Ser Leu Ser Arg His Asp His Ile His His His Gly
1               5                   10                  15

Lys

<210> SEQ ID NO 30
<211> LENGTH: 16
<212> TYPE: PRT
<213> ORGANISM: Artificial Sequence
<220> FEATURE:
<223> OTHER INFORMATION: fluorescent-labeled peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (16)..(16)
<223> OTHER INFORMATION: residue at this location is derivatized to
      N(epsilon)-[fluorescein-5(6)-carbonyl]-lysinamide

<400> SEQUENCE: 30

Ser His Ser Asp Phe Thr Lys Thr Ser Pro Leu Gly Ile His Gly Lys
1               5                   10                  15

<210> SEQ ID NO 31
<211> LENGTH: 17
<212> TYPE: PRT
<213> ORGANISM: Artificial Sequence
<220> FEATURE:
<223> OTHER INFORMATION: fluorescent superimposed labeling of sciatic
      nerve
<220> FEATURE:
<221> NAME/KEY: MOD_RES
```

```
<222> LOCATION: (1)..(1)
<223> OTHER INFORMATION: ACETYLATION
<220> FEATURE:
<221> NAME/KEY: MISC_FEATURE
<222> LOCATION: (17)..(17)
<223> OTHER INFORMATION: residue at this position is modified to a
      (Cy5)-amide

<400> SEQUENCE: 31

Ser His Ser Asn Thr Gln Thr Leu Ala Lys Ala Pro Glu His Thr Gly
1               5                   10                  15

Cys

<210> SEQ ID NO 32
<211> LENGTH: 11
<212> TYPE: PRT
<213> ORGANISM: Artificial Sequence
<220> FEATURE:
<223> OTHER INFORMATION: JNK Inhibitor VI
<220> FEATURE:
<221> NAME/KEY: MOD_RES
<222> LOCATION: (11)..(11)
<223> OTHER INFORMATION: AMIDATION

<400> SEQUENCE: 32

Arg Pro Lys Arg Pro Thr Thr Leu Asn Leu Phe
1               5                   10

<210> SEQ ID NO 33
<211> LENGTH: 16
<212> TYPE: PRT
<213> ORGANISM: Artificial Sequence
<220> FEATURE:
<223> OTHER INFORMATION: SC 3036

<400> SEQUENCE: 33

Lys Lys His Thr Asp Asp Gly Tyr Met Pro Met Ser Pro Gly Val Ala
1               5                   10                  15

<210> SEQ ID NO 34
<211> LENGTH: 28
<212> TYPE: PRT
<213> ORGANISM: Artificial Sequence
<220> FEATURE:
<223> OTHER INFORMATION: NEMO-Binding Domain Binding Peptide

<400> SEQUENCE: 34

Asp Arg Gln Ile Lys Ile Trp Phe Gln Asn Arg Arg Met Lys Trp Lys
1               5                   10                  15

Lys Thr Ala Leu Asp Trp Ser Trp Leu Gln Thr Glu
            20                  25

<210> SEQ ID NO 35
<211> LENGTH: 26
<212> TYPE: PRT
<213> ORGANISM: Artificial Sequence
<220> FEATURE:
<223> OTHER INFORMATION: NF-kB SN50

<400> SEQUENCE: 35

Ala Ala Val Ala Leu Leu Pro Ala Val Leu Leu Ala Leu Leu Ala Pro
1               5                   10                  15

Val Gln Arg Lys Arg Gln Lys Leu Met Pro
            20                  25

<210> SEQ ID NO 36
<211> LENGTH: 29
```

```
<212> TYPE: PRT
<213> ORGANISM: Artificial Sequence
<220> FEATURE:
<223> OTHER INFORMATION: TIRAP Inhibitor Peptide

<400> SEQUENCE: 36

Arg Gln Ile Lys Ile Trp Phe Asn Arg Arg Met Lys Trp Lys Lys Leu
1               5                   10                  15

Gln Leu Arg Asp Ala Ala Pro Gly Gly Ala Ile Val Ser
            20                  25

<210> SEQ ID NO 37
<211> LENGTH: 4
<212> TYPE: PRT
<213> ORGANISM: Artificial Sequence
<220> FEATURE:
<223> OTHER INFORMATION: drug
<220> FEATURE:
<221> NAME/KEY: MISC_FEATURE
<222> LOCATION: (1)..(1)
<223> OTHER INFORMATION: residue at this location is modified with
      benzyloxycarbonyl
<220> FEATURE:
<221> NAME/KEY: MISC_FEATURE
<222> LOCATION: (2)..(2)
<223> OTHER INFORMATION: residue at this location is modified to the
      methyl ester
<220> FEATURE:
<221> NAME/KEY: MISC_FEATURE
<222> LOCATION: (4)..(4)
<223> OTHER INFORMATION: residue at this location is modified at the
      side chain to the methyl ester and the c-terminal COOH group to
      fluoromethyl ketone

<400> SEQUENCE: 37

Leu Glu His Asp
1

<210> SEQ ID NO 38
<211> LENGTH: 4
<212> TYPE: PRT
<213> ORGANISM: Artificial Sequence
<220> FEATURE:
<223> OTHER INFORMATION: drug
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: the c-terminal COOH group is modified to CHO

<400> SEQUENCE: 38

Leu Glu His Asp
1

<210> SEQ ID NO 39
<211> LENGTH: 4
<212> TYPE: PRT
<213> ORGANISM: Artificial Sequence
<220> FEATURE:
<223> OTHER INFORMATION: drug
<220> FEATURE:
<221> NAME/KEY: MISC_FEATURE
<222> LOCATION: (1)..(1)
<223> OTHER INFORMATION: residue at this location is modified with
      acetyl
<220> FEATURE:
<221> NAME/KEY: MISC_FEATURE
<222> LOCATION: (4)..(4)
<223> OTHER INFORMATION: the c-terminal COOH group is modified to CHO
```

-continued

```
<400> SEQUENCE: 39

Ile Glu Thr Asp
1

<210> SEQ ID NO 40
<211> LENGTH: 4
<212> TYPE: PRT
<213> ORGANISM: Artificial Sequence
<220> FEATURE:
<223> OTHER INFORMATION: drug
<220> FEATURE:
<221> NAME/KEY: MISC_FEATURE
<222> LOCATION: (1)..(1)
<223> OTHER INFORMATION: residue at this location is modified with
      benzyloxycarbonyl
<220> FEATURE:
<221> NAME/KEY: MISC_FEATURE
<222> LOCATION: (2)..(2)
<223> OTHER INFORMATION: residue at this location is modified to the
      methyl ester
<220> FEATURE:
<221> NAME/KEY: MISC_FEATURE
<222> LOCATION: (3)..(3)
<223> OTHER INFORMATION: residue at this location is modified at the
      side chain to the methyl ester and the c-terminus to fluoromethyl
      ketone

<400> SEQUENCE: 40

Ile Glu Thr Asp
1

<210> SEQ ID NO 41
<211> LENGTH: 4
<212> TYPE: PRT
<213> ORGANISM: Artificial Sequence
<220> FEATURE:
<223> OTHER INFORMATION: drug
<220> FEATURE:
<221> NAME/KEY: MISC_FEATURE
<222> LOCATION: (1)..(1)
<223> OTHER INFORMATION: residue at this location is modified with FAM
<220> FEATURE:
<221> NAME/KEY: MISC_FEATURE
<222> LOCATION: (4)..(4)
<223> OTHER INFORMATION: the c-terminal COOH group is modified to
      fluoromethyl ketone

<400> SEQUENCE: 41

Leu Glu His Asp
1

<210> SEQ ID NO 42
<211> LENGTH: 4
<212> TYPE: PRT
<213> ORGANISM: Artificial Sequence
<220> FEATURE:
<223> OTHER INFORMATION: drug
<220> FEATURE:
<221> NAME/KEY: MISC_FEATURE
<222> LOCATION: (1)..(1)
<223> OTHER INFORMATION: residue at this location modified with FAM
<220> FEATURE:
<221> NAME/KEY: MISC_FEATURE
<222> LOCATION: (4)..(4)
<223> OTHER INFORMATION: the c-terminal COOH group is modified to
      fluoromethyl ketone

<400> SEQUENCE: 42

Leu Glu Thr Asp
1

<210> SEQ ID NO 43
```

```
<211> LENGTH: 16
<212> TYPE: PRT
<213> ORGANISM: Artificial Sequence
<220> FEATURE:
<223> OTHER INFORMATION: SC 3036

<400> SEQUENCE: 43

Lys Lys His Thr Asp Asp Gly Tyr Met Pro Met Ser Pro Gly Val Ala
1               5                   10                  15

<210> SEQ ID NO 44
<211> LENGTH: 12
<212> TYPE: PRT
<213> ORGANISM: Artificial Sequence
<220> FEATURE:
<223> OTHER INFORMATION: control sequence

<400> SEQUENCE: 44

Ser Thr Ala Arg Asp Leu Trp Pro His Gly Lys Glu
1               5                   10

<210> SEQ ID NO 45
<211> LENGTH: 17
<212> TYPE: PRT
<213> ORGANISM: Artificial Sequence
<220> FEATURE:
<223> OTHER INFORMATION: fluorescent-labeled peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (10)..(10)
<223> OTHER INFORMATION: ACETYLATION
<220> FEATURE:
<221> NAME/KEY: MISC_FEATURE
<222> LOCATION: (17)..(17)
<223> OTHER INFORMATION: residue at this location is derivatized to
      N(epsilon)-[fluorescein-5(6)-carbonyl]-lysinamide

<400> SEQUENCE: 45

Ser His Ser Asn Thr Gln Thr Leu Ala Lys Ala Pro Glu His Thr Gly
1               5                   10                  15

Lys

<210> SEQ ID NO 46
<211> LENGTH: 17
<212> TYPE: PRT
<213> ORGANISM: Artificial Sequence
<220> FEATURE:
<223> OTHER INFORMATION: fluorescent-labeled peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (17)..(17)
<223> OTHER INFORMATION: residue at this location is modified to a
      (5,6FAM)-amide

<400> SEQUENCE: 46

Ser His Ser Asn Thr Gln Thr Leu Ala Lys Ala Pro Glu His Thr Gly
1               5                   10                  15

Cys

<210> SEQ ID NO 47
<211> LENGTH: 17
<212> TYPE: PRT
```

```
<213> ORGANISM: Artificial Sequence
<220> FEATURE:
<223> OTHER INFORMATION: fluorescent-labeled peptide
<220> FEATURE:
<221> NAME/KEY: MISC_FEATURE
<222> LOCATION: (17)..(17)
<223> OTHER INFORMATION: residue at this location is modified to a
      (5,6FAM)-amide

<400> SEQUENCE: 47

Ser His Ser Asn Thr Gln Thr Leu Ala Lys Ala Pro Glu His Thr Gly
1               5                   10                  15

Cys

<210> SEQ ID NO 48
<211> LENGTH: 17
<212> TYPE: PRT
<213> ORGANISM: Artificial Sequence
<220> FEATURE:
<223> OTHER INFORMATION: fluorescent-labeled peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (17)..(17)
<223> OTHER INFORMATION: a residue at this location modified with
      IR800CW

<400> SEQUENCE: 48

Ser His Ser Asn Thr Gln Thr Leu Ala Lys Ala Pro Glu His Thr Gly
1               5                   10                  15

Cys

<210> SEQ ID NO 49
<211> LENGTH: 17
<212> TYPE: PRT
<213> ORGANISM: Artificial Sequence
<220> FEATURE:
<223> OTHER INFORMATION: fluorescent-labeled peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (17)..(17)
<223> OTHER INFORMATION: residue at this location is modified to a
      TAMRA-amide

<400> SEQUENCE: 49

Ser His Ser Asn Thr Gln Thr Leu Ala Lys Ala Pro Glu His Thr Gly
1               5                   10                  15

Cys

<210> SEQ ID NO 50
<211> LENGTH: 17
<212> TYPE: PRT
<213> ORGANISM: Artificial Sequence
<220> FEATURE:
<223> OTHER INFORMATION: fluorescent-labeled peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (17)..(17)
<223> OTHER INFORMATION: residue at this location is modified to a Texas
      Red-amide
```

<400> SEQUENCE: 50

Ser His Ser Asn Thr Gln Thr Leu Ala Lys Ala Pro Glu His Thr Gly
1               5                   10                  15

Cys

<210> SEQ ID NO 51
<211> LENGTH: 17
<212> TYPE: PRT
<213> ORGANISM: Artificial Sequence
<220> FEATURE:
<223> OTHER INFORMATION: fluorescent-labeled peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (17)..(17)
<223> OTHER INFORMATION: residue at this location is modified with a
      indocyanine green derivative

<400> SEQUENCE: 51

Ser His Ser Asn Thr Gln Thr Leu Ala Lys Ala Pro Glu His Thr Gly
1               5                   10                  15

Cys

<210> SEQ ID NO 52
<211> LENGTH: 17
<212> TYPE: PRT
<213> ORGANISM: Artificial Sequence
<220> FEATURE:
<223> OTHER INFORMATION: fluorescent-labeled peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (17)..(17)
<223> OTHER INFORMATION: residue at this location modified with a
      heptamethinecyanine derivative

<400> SEQUENCE: 52

Ser His Ser Asn Thr Gln Thr Leu Ala Lys Ala Pro Glu His Thr Gly
1               5                   10                  15

Cys

<210> SEQ ID NO 53
<211> LENGTH: 100
<212> TYPE: DNA
<213> ORGANISM: Artificial Sequence
<220> FEATURE:
<223> OTHER INFORMATION: Library 1: (N60) EcoR1-N60-EcoR1
<220> FEATURE:
<221> NAME/KEY: misc_feature
<222> LOCATION: (21)..(80)
<223> OTHER INFORMATION: n is a, c, g, or t

<400> SEQUENCE: 53
ggacgcggaa ttccgactcg nnnnnnnnnn nnnnnnnnnn nnnnnnnnnn nnnnnnnnnn     60
nnnnnnnnnn nnnnnnnnnn ctcatcggaa ttccgcgtcc                          100

<210> SEQ ID NO 54
<211> LENGTH: 89
<212> TYPE: DNA
<213> ORGANISM: Artificial Sequence
<220> FEATURE:

<223> OTHER INFORMATION: Library 2 (N50)-EcoR1-N50-EcoR1
<220> FEATURE:
<221> NAME/KEY: misc_feature
<222> LOCATION: (21)..(70)
<223> OTHER INFORMATION: n is a, c, g, or t

<400> SEQUENCE: 54
ggacgcggaa ttccgattac nnnnnnnnnn nnnnnnnnnn nnnnnnnnnn nnnnnnnnnn    60
nnnnnnnnnn cagaccggaa ttccgctcc                                      89

<210> SEQ ID NO 55
<211> LENGTH: 120
<212> TYPE: DNA
<213> ORGANISM: Artificial Sequence
<220> FEATURE:
<223> OTHER INFORMATION: Library 3 (3N20) EcoR1-N20-Xba-N20-Xba-N20EcoR1
<220> FEATURE:
<221> NAME/KEY: misc_feature
<222> LOCATION: (21)..(40)
<223> OTHER INFORMATION: n is a, c, g, or t
<220> FEATURE:
<221> NAME/KEY: misc_feature
<222> LOCATION: (51)..(70)
<223> OTHER INFORMATION: n is a, c, g, or t
<220> FEATURE:
<221> NAME/KEY: misc_feature
<222> LOCATION: (81)..(100)
<223> OTHER INFORMATION: n is a, c, g, or t

<400> SEQUENCE: 55
ggacgcggaa ttccgccgtc nnnnnnnnnn nnnnnnnnnn gctctagagc nnnnnnnnnn    60
nnnnnnnnnn gctctagagc nnnnnnnnnn nnnnnnnnnn gataccggaa ttccgcgtcc   120

<210> SEQ ID NO 56
<211> LENGTH: 63
<212> TYPE: DNA
<213> ORGANISM: Artificial Sequence
<220> FEATURE:
<223> OTHER INFORMATION: MC-M2-a

<400> SEQUENCE: 56
gaattccggt ctggaggacc ggatggcaaa aatatctaaa aaacacagaa taaaacgtta    60
ttg                                                                  63

<210> SEQ ID NO 57
<211> LENGTH: 13
<212> TYPE: DNA
<213> ORGANISM: Artificial Sequence
<220> FEATURE:
<223> OTHER INFORMATION: MC-m2-a

<400> SEQUENCE: 57
gtaatcggaa ttc                                                       13

<210> SEQ ID NO 58
<211> LENGTH: 43
<212> TYPE: DNA
<213> ORGANISM: Artificial Sequence
<220> FEATURE:
<223> OTHER INFORMATION: MC-m2-b

<400> SEQUENCE: 58
gaattccgat taccacaaat tcgttacatg ctcctctatc gcg                      43

<210> SEQ ID NO 59
<211> LENGTH: 16
<212> TYPE: DNA

```
<213> ORGANISM: Artificial Sequence
<220> FEATURE:
<223> OTHER INFORMATION: MC-m2-b

<400> SEQUENCE: 59
ccttccttcc gtccgc                                                    16

<210> SEQ ID NO 60
<211> LENGTH: 13
<212> TYPE: DNA
<213> ORGANISM: Artificial Sequence
<220> FEATURE:
<223> OTHER INFORMATION: MC-m2-b

<400> SEQUENCE: 60
cagaccggaa ttc                                                       13

<210> SEQ ID NO 61
<211> LENGTH: 13
<212> TYPE: DNA
<213> ORGANISM: Artificial Sequence
<220> FEATURE:
<223> OTHER INFORMATION: MC-m2-c

<400> SEQUENCE: 61
gaattccggt ctg                                                       13

<210> SEQ ID NO 62
<211> LENGTH: 46
<212> TYPE: DNA
<213> ORGANISM: Artificial Sequence
<220> FEATURE:
<223> OTHER INFORMATION: MC-m2-c

<400> SEQUENCE: 62
ggaacagacc ggcctcttat tgtggtttcg gcttggttag cgggtg                   46

<210> SEQ ID NO 63
<211> LENGTH: 13
<212> TYPE: DNA
<213> ORGANISM: Artificial Sequence
<220> FEATURE:
<223> OTHER INFORMATION: MC-m2-c

<400> SEQUENCE: 63
gtaatcggaa ttc                                                       13

<210> SEQ ID NO 64
<211> LENGTH: 14
<212> TYPE: DNA
<213> ORGANISM: Artificial Sequence
<220> FEATURE:
<223> OTHER INFORMATION: MC-m2-d

<400> SEQUENCE: 64
ggaattccga ttac                                                      14

<210> SEQ ID NO 65
<211> LENGTH: 62
<212> TYPE: DNA
<213> ORGANISM: Artificial Sequence
<220> FEATURE:
<223> OTHER INFORMATION: MC-m2-d

<400> SEQUENCE: 65
cgacgtgtct accttcattt actgtcccca tcgtccccg ggttggtccc agaccggaat      60
``` tc                                                                62

<210> SEQ ID NO 66
<211> LENGTH: 13
<212> TYPE: DNA
<213> ORGANISM: Artificial Sequence
<220> FEATURE:
<223> OTHER INFORMATION: MC-m2-e

<400> SEQUENCE: 66
gaattccgat tac                                                    13

<210> SEQ ID NO 67
<211> LENGTH: 51
<212> TYPE: DNA
<213> ORGANISM: Artificial Sequence
<220> FEATURE:
<223> OTHER INFORMATION: MC-m2-e

<400> SEQUENCE: 67
catagttatg tcgtgtctct aggtcatcct tcctcgtcat tcccggtccc a           51

<210> SEQ ID NO 68
<211> LENGTH: 11
<212> TYPE: DNA
<213> ORGANISM: Artificial Sequence
<220> FEATURE:
<223> OTHER INFORMATION: MC-m2-e

<400> SEQUENCE: 68
gaccggaatt c                                                      11

<210> SEQ ID NO 69
<211> LENGTH: 13
<212> TYPE: DNA
<213> ORGANISM: Artificial Sequence
<220> FEATURE:
<223> OTHER INFORMATION: MC-m3-a

<400> SEQUENCE: 69
gaattccgcc gtc                                                    13

<210> SEQ ID NO 70
<211> LENGTH: 20
<212> TYPE: DNA
<213> ORGANISM: Artificial Sequence
<220> FEATURE:
<223> OTHER INFORMATION: MC-m3-a

<400> SEQUENCE: 70
ggcgggacct gggctatgtt                                             20

<210> SEQ ID NO 71
<211> LENGTH: 9
<212> TYPE: DNA
<213> ORGANISM: Artificial Sequence
<220> FEATURE:
<223> OTHER INFORMATION: MC-m3-a

<400> SEQUENCE: 71 gctttagag                                                          9

<210> SEQ ID NO 72
<211> LENGTH: 20
<212> TYPE: DNA
<213> ORGANISM: Artificial Sequence
<220> FEATURE:

<223> OTHER INFORMATION: MC-m3-a

<400> SEQUENCE: 72
cccggaaggc aggggtaata                                           20

<210> SEQ ID NO 73
<211> LENGTH: 9
<212> TYPE: DNA
<213> ORGANISM: Artificial Sequence
<220> FEATURE:
<223> OTHER INFORMATION: MC-m3-a

<400> SEQUENCE: 73 gctctagag                                                        9

<210> SEQ ID NO 74
<211> LENGTH: 21
<212> TYPE: DNA
<213> ORGANISM: Artificial Sequence
<220> FEATURE:
<223> OTHER INFORMATION: MC-m3-a

<400> SEQUENCE: 74
ccaggagagg tgtgggggt g                                          21

<210> SEQ ID NO 75
<211> LENGTH: 13
<212> TYPE: DNA
<213> ORGANISM: Artificial Sequence
<220> FEATURE:
<223> OTHER INFORMATION: MC-m3-a

<400> SEQUENCE: 75
gataccggaa ttc                                                  13

<210> SEQ ID NO 76
<211> LENGTH: 13
<212> TYPE: DNA
<213> ORGANISM: Artificial Sequence
<220> FEATURE:
<223> OTHER INFORMATION: MC-m3-b

<400> SEQUENCE: 76
gaattccgcc gtc                                                  13

<210> SEQ ID NO 77
<211> LENGTH: 20
<212> TYPE: DNA
<213> ORGANISM: Artificial Sequence
<220> FEATURE:
<223> OTHER INFORMATION: MC-m3-b

<400> SEQUENCE: 77
ggcggacgac cctcagttcg                                           20

<210> SEQ ID NO 78
<211> LENGTH: 10
<212> TYPE: DNA
<213> ORGANISM: Artificial Sequence
<220> FEATURE:
<223> OTHER INFORMATION: MC-m3-b

<400> SEQUENCE: 78
gctctaggag                                                      10

<210> SEQ ID NO 79

```
<211> LENGTH: 21
<212> TYPE: DNA
<213> ORGANISM: Artificial Sequence
<220> FEATURE:
<223> OTHER INFORMATION: MC-m3-b

<400> SEQUENCE: 79
caatattaat cctcatgggc c                                              21

<210> SEQ ID NO 80
<211> LENGTH: 9
<212> TYPE: DNA
<213> ORGANISM: Artificial Sequence
<220> FEATURE:
<223> OTHER INFORMATION: MC-m3-b

<400> SEQUENCE: 80 gctctagag                                                             9

<210> SEQ ID NO 81
<211> LENGTH: 21
<212> TYPE: DNA
<213> ORGANISM: Artificial Sequence
<220> FEATURE:
<223> OTHER INFORMATION: MC-m3-b

<400> SEQUENCE: 81
ctcgcacttt tttgtaatgt t                                              21

<210> SEQ ID NO 82
<211> LENGTH: 14
<212> TYPE: DNA
<213> ORGANISM: Artificial Sequence
<220> FEATURE:
<223> OTHER INFORMATION: MC-m3-b

<400> SEQUENCE: 82
gataccggaa ttcc                                                      14

<210> SEQ ID NO 83
<211> LENGTH: 13
<212> TYPE: DNA
<213> ORGANISM: Artificial Sequence
<220> FEATURE:
<223> OTHER INFORMATION: m1a

<400> SEQUENCE: 83
gaattccgat gag                                                       13

<210> SEQ ID NO 84
<211> LENGTH: 60
<212> TYPE: DNA
<213> ORGANISM: Artificial Sequence
<220> FEATURE:
<223> OTHER INFORMATION: m1a

<400> SEQUENCE: 84
cacaatctca accacgtccc caagcaatgt agcttccacg atttatggcc cgactcgtcc    60

<210> SEQ ID NO 85
<211> LENGTH: 14
<212> TYPE: DNA
<213> ORGANISM: Artificial Sequence
<220> FEATURE:
<223> OTHER INFORMATION: m1a

<400> SEQUENCE: 85
```

-continued

```
cgagtcggaa ttcc                                                         14

<210> SEQ ID NO 86
<211> LENGTH: 13
<212> TYPE: DNA
<213> ORGANISM: Artificial Sequence
<220> FEATURE:
<223> OTHER INFORMATION: m1b

<400> SEQUENCE: 86
gaattccgat gag                                                          13

<210> SEQ ID NO 87
<211> LENGTH: 60
<212> TYPE: DNA
<213> ORGANISM: Artificial Sequence
<220> FEATURE:
<223> OTHER INFORMATION: m1b

<400> SEQUENCE: 87
cacaatctca accacgtccc caagcaatgt agcttccacg atttatggcc cgactcgtcc      60

<210> SEQ ID NO 88
<211> LENGTH: 14
<212> TYPE: DNA
<213> ORGANISM: Artificial Sequence
<220> FEATURE:
<223> OTHER INFORMATION: m1b

<400> SEQUENCE: 88
cgagtcggaa ttcc                                                         14

<210> SEQ ID NO 89
<211> LENGTH: 12
<212> TYPE: PRT
<213> ORGANISM: Artificial Sequence
<220> FEATURE:
<223> OTHER INFORMATION: structural isomer of fluorescent-labeled
      peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (12)..(12)
<223> OTHER INFORMATION: modified by a FAM-amide

<400> SEQUENCE: 89

Asn Thr Gln Thr Leu Ala Lys Ala Pro Glu His Thr
1               5                   10
```

What is claimed is:

1. A targeting molecule comprising a peptide that specifically binds to a peripheral nervous system (PNS) neuron or nerve, or component of either, wherein the peptide is at least 85% homologous to a peptide comprising NTQTLAKAPEHT (SEQ ID NO:4).

2. The molecule of claim 1, further comprising a drug.

3. The molecule of claim 1, further comprising a drug selected from the group consisting of: an antihistamine, a GABA receptor modulator, a neurotransmitter reuptake inhibitor, a local anesthetic, an anticholinergic, a sodium channel blocker, a calcium channel blocker, a thyrotropin-releasing hormone, a γ-secretase inhibitor, an AMPA receptor agonist or antagonist, an NMDA receptor agonist or antagonist, an mGlu receptor agonist or antagonist, a growth factor, an antiemetic agent, a corticosteroid; a cytotoxic agent; an antioxidant, an iron chelator, a mitochondrial modulator, a sirtuin modulator, a nitric oxide (NO) and/or nitric oxide synthase (NOS) modulator, a potassium channel agonist or antagonist, a purigenic receptor agonist or antagonist and combinations thereof.

4. The molecule of claim 1, further comprising a drug selected from the group consisting of: benzocaine, cardcaine, cinchocaine, cyclomethycaine, lidocaine, pritocaine, propxycaine, proparacaine, tetracaine, tocainide, trimecaine, methotrexate, cyclophosphamide, thalidomide, paclitaxel, pemetrexed, pentostatin, pipobroman, pixantrone, plicamycin, procarbazine, raltitrexed, rebeccamycin, rubitecan, SN-38, salinosporamide A, satraplatin, streptozotocin, swainsonine, tariquidar, taxane, tegafur-uracil, temozolomide, testolactone, thioTEPA, tioguanine, topotecan, trabectedin, tretinoin, triplatin tetranitrate, tris(2-chloroethyl)amine, troxacitabine, uracil mustard, valrubicin, vinblastine, vincristine, vinorelbine, vorinostat, zosuquidar, carbamazepine, oxcarbazepine, phenytein, valproic acid, sodium valproate, cinnarizine, flunarizine, nimodipine, brain-derived neurotrophic factor (BDNF), ciliary neurotrophic factor (CNTF), gilal cell-line derived neurotrophic factor (GDNF), neurotrophin-3, neurotrophin-4, fibroblast growth factor (FGF) receptor, insulin-like growth factor (IGF) and combinations thereof.

5. The molecule of claim 1, further comprising a fluorescent moiety.

6. The molecule of claim 1, further comprising a fluorescent moiety selected from the group consisting of: a fluorescent dye, a fluorescent peptide, a fluorescent dye and combination thereof.

7. The molecule of claim 1, further comprising a fluorescent moiety selected from the group consisting of: a xanthene a bimane a coumarin an aromatic amines a benzofuran a fluorescent cyanine a carbazole a dicyanomethylene pyrane polymethine oxabenzanthrane pyrylium carbostyl perylene acridone quinacridone rubrene anthracene coronene phenanthrecene pyrene butadiene stilbene porphyrin pthalocyanine lanthanide metal chelate complexes and rare-earth metal chelate complexes.

8. The molecule of claim 1, further comprising a fluorescent moiety selected from the group consisting of: 5-carboxyfluorescein, fluorescein-5-isothiocyanate, 6-carboxyfluorescein, tetramethylrhodamine-6-isothiocyanate, 5-carboxytetramethylrhodamine 5-carboxy rhodol derivatives tetramethyl and tetraethyl rhodamine diphenyldimethyl and diphenyldiethyl rhodamine dinaphthyl rhodamine; rhodamine 101 sulfonyl chloride Cy3, Cy3B, Cy3.5, Cy5, Cy5~5, Cy 7, indocyanine green, IRS00CW and combinations thereof.

9. A method of identifying a PNS neuron or nerve, comprising contacting the PNS neuron or nerve with a targeting molecule comprising (a) a peptide that specifically binds to the neuron or nerve, or component of either, and (b) a fluorescent moiety, wherein the peptide is at least 85% homologous to a peptide comprising NTQTLAKAPEHT (SEQ ID NO:4).

10. The method of claim 9, wherein the fluorescent moiety selected from the group consisting of: a fluorescent dye, a fluorescent peptide, a fluorescent dye and combinations thereof.

11. The method of claim 9, wherein the fluorescent moiety selected from the group consisting of: a xanthene a bimane a coumarin an aromatic amines a benzofuran a fluorescent cyanine a carbazole a dicyanomethylene pyrane polymethine oxabenzanthrane pyrylium carbostyl perylene acridone quinacridone rubrene anthracene coronene phenanthrecene pyrene butadiene stilbene porphyrin pthalocyanine lanthanide metal chelate complexes and rare-earth metal chelate complexes.

12. The method of claim 9, wherein the fluorescent moiety selected from the group consisting of: 5-carboxyfluorescein, fluorescein-5-isothiocyanate, 6-carboxyfluorescein, tetramethylrhodamine-6-isothiocyanate, 5-carboxytetramethylrhodamine 5-carboxy rhodol derivatives tetramethyl and tetraethyl rhodamine diphenyldimethyl and diphenyldiethyl rhodamine dinaphthyl rhodamine rhodamine 101 sulfonyl chloride Cy3, Cy3B, Cy3.5, Cy5, Cy5~5, Cy 7, indocyanine green, IRS00CW and combinations thereof.

13. A method of delivering a drug to a PNS neuron or nerve, comprising contacting the PNS neuron or nerve with a targeting molecule comprising (a) a peptide that specifically binds to the neuron or nerve, or component of either, and (b) a drug, wherein the peptide is at least 85% homologous to a peptide comprising NTQTLAKAPEHT (SEQ ID NO:4).

14. The method of claim 13, wherein the drug is selected from the group consisting of: an antihistamine, a GABA receptor modulator, a neurotransmitter reuptake inhibitor, a local anesthetic, an anticholinergic, a sodium channel blocker, a calcium channel blocker, a thyrotropin-releasing hormone, a y-secretase inhibitor, an AMPA receptor agonist or antagonist, an NMDA receptor agonist or antagonist, an mGlu receptor agonist or antagonist, a growth factor, an antiemetic agent, a corticosteroid; a cytotoxic agent; an antioxidant, an iron chelator, a mitochondrial modulator, a sirtuin modulator, a nitric oxide (NO) and/or nitric oxide synthase (NOS) modulator, a potassium channel agonist or antagonist, a purigenic receptor agonist or antagonist and combinations thereof.

15. The method of claim 13, wherein the drug is selected from the group consisting of: benzocaine, cardcaine, cinchocaine, cyclomethycaine, lidocaine, pritocaine, propxycaine, proparacaine, tetracaine, tocainide, trimecaine, methotrexate, cyclophosphamide, thalidomide, paclitaxel, pemetrexed, pentostatin, pipobroman, pixantrone, plicamycin, procarbazine, raltitrexed, rebeccamycin, rubitecan, SN-38, salinosporamide A, satraplatin, streptozotocin, swainsonine, tariquidar, taxane, tegafur-uracil, temozolomide, testolactone, thioTEPA, tioguanine, topotecan, trabectedin, tretinoin, triplatin tetranitrate, tris(2-chloroethyl)amine, troxacitabine, uracil mustard, valrubicin, vinblastine, vincristine, vinorelbine, vorinostat, zosuquidar, carbamazepine, oxcarbazepine, phenytein, valproic acid, sodium valproate, cinnarizine, flunarizine, nimodipine, brain-derived neurotrophic factor (BDNF), ciliary neurotrophic factor (CNTF), gilal cell-line derived neurotrophic factor (GDNF), neurotrophin-3, neurotrophin-4, fibroblast growth factor (FGF) receptor, insulin-like growth factor (IGF) and combinations thereof.

16. A pharmaceutical composition comprising: (a) a peptide that specifically binds to a PNS neuron, nerve, or component of either, and (b) a pharmaceutically acceptable excipient, wherein the peptide is at least 85% homologous to a peptide comprising NTQTLAKAPEHT (SEQ ID NO:4).

17. The composition of claim 16, wherein the peptide is bound to a drug or fluorescent moiety.

* * * * *